(12) United States Patent
Kessler et al.

(10) Patent No.: US 9,364,418 B2
(45) Date of Patent: Jun. 14, 2016

(54) WATER-RESISTANT COSMETIC FORMULATIONS COMPRISING A HYDROPHOBICALLY MODIFIED VINYLPYRROLIDONE COPOLYMER

(75) Inventors: Veronique Kessler, Basel (CH); Maximilian Angel, Schifferstadt (DE); Klemens Mathauer, Heidelberg (DE)

(73) Assignee: BASF SE, Ludwigshafen (DE)

( * ) Notice: Subject to any disclaimer, the term of this patent is extended or adjusted under 35 U.S.C. 154(b) by 7 days.

(21) Appl. No.: 13/519,897

(22) PCT Filed: Jan. 12, 2011

(86) PCT No.: PCT/EP2011/050291
§ 371 (c)(1),
(2), (4) Date: Jul. 23, 2012

(87) PCT Pub. No.: WO2011/086073
PCT Pub. Date: Jul. 21, 2011

(65) Prior Publication Data
US 2012/0276027 A1    Nov. 1, 2012

(30) Foreign Application Priority Data

Jan. 14, 2010  (EP) .................................... 10150699

(51) Int. Cl.
| | | |
|---|---|---|
| *A61Q 1/06* | (2006.01) | |
| *A61Q 1/10* | (2006.01) | |
| *A61Q 17/04* | (2006.01) | |
| *A61K 8/81* | (2006.01) | |

(52) U.S. Cl.
CPC ............... *A61K 8/8182* (2013.01); *A61Q 1/06* (2013.01); *A61Q 1/10* (2013.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 3,405,084 A | * | 10/1968 | Bohac et al. | 424/47 |
| 3,423,381 A | | 1/1969 | Merijan | |
| 3,880,813 A | * | 4/1975 | Guse et al. | 526/321 |
| 4,364,972 A | * | 12/1982 | Moon | 427/516 |
| 5,219,559 A | | 6/1993 | Kopolow | |
| 6,010,707 A | | 1/2000 | Philippe et al. | |
| 6,075,107 A | | 6/2000 | Kothrade et al. | |
| 6,106,809 A | * | 8/2000 | Bhatt et al. | 424/45 |
| 6,132,705 A | | 10/2000 | Schehlmann et al. | |
| 6,436,440 B1 | | 8/2002 | Meffert et al. | |
| 6,482,400 B1 | | 11/2002 | Collin | |
| 8,003,738 B2 | | 8/2011 | Bouillo | |
| 2002/0110571 A1 | | 8/2002 | Kanji | |
| 2003/0202953 A1 | * | 10/2003 | Tamareselvy et al. | 424/70.16 |
| 2004/0005279 A1 | | 1/2004 | Lorant | |
| 2005/0112080 A1 | | 5/2005 | Cao et al. | |
| 2006/0083696 A1 | | 4/2006 | Yu et al. | |
| 2011/0117142 A1 | | 5/2011 | Kolter | |
| 2011/0189113 A1 | | 8/2011 | Ross | |
| 2011/0263786 A1 | | 10/2011 | Angel | |
| 2012/0076858 A1 | | 3/2012 | Kolter | |
| 2012/0214917 A1 | | 8/2012 | Kolter | |

FOREIGN PATENT DOCUMENTS

| | | |
|---|---|---|
| DE | 19627204 A1 | 1/1998 |
| DE | 19814730 A1 | 10/1999 |
| EP | 0277426 A1 * | 8/1988 |
| EP | 0815829 A1 | 1/1998 |
| EP | 0876819 A1 | 11/1998 |
| EP | 0953358 A1 | 11/1999 |
| EP | 1647268 A1 | 4/2006 |
| EP | 1669374 A1 | 6/2006 |
| WO | 0101936 A1 | 1/2001 |
| WO | 0249586 A2 | 6/2002 |
| WO | 2009023662 A2 | 2/2009 |

* cited by examiner

*Primary Examiner* — Ali Soroush
(74) *Attorney, Agent, or Firm* — Marshall, Gerstein & Borun LLP

(57) ABSTRACT

The present invention relates to the use of copolymers comprising N-vinylpyrrolidone and a hydrophobically modified acrylic acid derivative as agents for improving the water resistance of a cosmetic formulation, and to the use of these copolymers in sunscreen compositions for increasing the sun protection factor, and furthermore the present invention relates to cosmetic formulations comprising these copolymers.

13 Claims, No Drawings

WATER-RESISTANT COSMETIC FORMULATIONS COMPRISING A HYDROPHOBICALLY MODIFIED VINYLPYRROLIDONE COPOLYMER The present invention relates to the use of copolymers comprising N-vinylpyrrolidone and a hydrophobically modified acrylic acid derivative as means for improving the water resistance of a cosmetic formulation, and to the use of these copolymers in sunscreen compositions for increasing the sun protection factor, and furthermore the present invention relates to cosmetic formulations comprising these copolymers.

For cosmetic formulations which are applied, for example, to the skin, good water resistance is often desirable. The consumer expects that for example a make-up composition for the eyes such as mascara is washed away neither by tear fluid nor by drops of perspiration. Similarly, the consumer expects an applied sunscreen composition to largely remain on the skin during sweaty sporting activity or during swimming outdoors in order to protect the user against the harmful UV rays during said activities. Although many cosmetic formulations already lay claim to the properties of waterproofness or water resistance, there is still a need for products with longer-lasting water resistance associated with improved skin feel upon application of the cosmetic formulation. Many of the commercially available cosmetic formulations which lay claim to water resistance are perceived by the user upon application as being waxy, greasy, sticky and oily. Consumers thus demand not only cosmetic products with improved water resistance, but also products which, upon application, leave behind a supple and soft impression and do not feel waxy, greasy or oily.

In order to achieve the water resistance of a cosmetic formulation, polymers are often added to the cosmetic formulations. The disadvantage of the known compositions, however, is often the difficult handleability and incorporability into the corresponding cosmetic formulations. The manufacturers of cosmetic formulations therefore expect a new feed material for increasing water resistance to be able to be incorporated easily into the formulation, if desired both into the oil phase and also into the aqueous phase of a cosmetic formulation, it being possible to dispense with heating, a neutralization step or other special processing steps.

Copolymers of N-vinylpyrrolidone and α-olefins and their use in cosmetic formulations are described, for example, in U.S. Pat. No. 5,219,559 and in U.S. Pat. No. 3,423,381. For example, the poly(N-vinylpyrrolidone/hexadecene) copolymer or the poly(N-vinylpyrrolidone/eicosene) copolymer with the trade names Antaron V-216, and Antaron V-220 are often used in cosmetic formulations for producing water resistance. These two copolymers are oil-soluble, Antaron V-216 being a viscous liquid and Antaron V-220 being a waxy solid. On account of their physical properties, the two polymers cannot be incorporated as desired into a cosmetic formulation. Moreover, when using the poly(N-vinylpyrrolidone/eicosene) copolymer, the viscosity of the cosmetic formulation is often increased in an undesired manner. Furthermore, the resulting cosmetic formulations, when applied to the skin, often leave behind a sticky and oily impression.

EP 0 815 829 proposes polymers and copolymers based on a $C_1$-$C_{30}$-(meth)acrylic acid ester which are able to improve the water resistance and wet abrasion resistance of a cosmetic formulation.

US 2005/01412080 proposes copolymers based on at least two acrylates in order to improve the water resistance of a cosmetic formulation.

The object of the present invention was to arrive, in a simple and cost-effective manner, at cosmetic formulations having good water resistance which, upon application, leave behind a supple and soft impression and do not feel waxy, greasy or oily. Furthermore, the substance improving the water resistance of the cosmetic formulation should be able to be incorporated easily and flexibly into the cosmetic formulation.

This object is achieved through the use of copolymers comprising a) 40 to 95% by weight of N-vinylpyrrolidone and b) 5 to 60% by weight of a hydrophobically modified acrylic acid derivative as agents for improving the water resistance of a cosmetic formulation.

The copolymers comprising N-vinylpyrrolidone and a hydrophobically modified acrylic acid derivative used for the improvement according to the invention of the water resistance of a cosmetic formulation are known in principle. Processes for the preparation of such copolymers are likewise known.

EP 0 876 819 proposes the use of copolymers comprising N-vinylpyrrolidone and a long-chain alkyl ester of (meth) acrylic acid as surface-active substances in preparations of water-insoluble substances, such as, for example, the pharmaceutical active ingredient diazepam.

EP 0 953 358 proposes the use of copolymers comprising N-vinylpyrrolidone and a long-chain alkyl ester of (meth) acrylic acid as matrix material for producing solid pharmaceutical and cosmetic administration forms, such as, for example, tablets.

EP 1 669 374 describes a process for the preparation of aqueous dispersions of copolymers, for example of the monomers N-vinylpyrrolidone and stearyl methacrylate.

The copolymers used in the use according to the invention for improving water resistance comprise a) 40 to 95% by weight, preferably 50 to 85% by weight, particularly preferably 60 to 80% by weight, in particular 65 to 75% by weight, of N-vinylpyrrolidone and b) 5 to 60% by weight, preferably 15 to 50% by weight, particularly preferably 20 to 40% by weight, in particular 25 to 35% by weight, of a hydrophobically modified acrylic acid derivative.

Preferably, the copolymers used in the use according to the invention for improving water resistance consist to more than 80% by weight, particularly preferably to more than 90% by weight, very particularly preferably to more than 96% by weight, in particular to more than 99% by weight, of N-vinylpyrrolidone and the hydrophobically modified acrylic acid derivative.

The hydrophobically modified acrylic acid derivative is preferably those compounds of acrylic acid in which either the hydrogen radical in the α position is replaced by a hydrocarbon radical, such as, for example, an alkyl radical or aryl radical, preferably a $C_1$ to $C_6$-alkyl radical, in particular methyl, and/or the carbonyl group in the second α position is substituted with an alkoxy radical having at least 4 carbon atoms.

The hydrophobically modified acrylic acid derivative is particularly preferably an acrylic acid ester or methacrylic acid ester of the formula I,

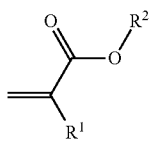

(I)

in which
R$^1$ is hydrogen or methyl, in particular methyl, and
R$^2$ is C$_8$ to C$_{32}$-alkyl, preferably C$_{10}$ C$_{28}$-alkyl, particularly preferably C$_{12}$ to C$_{24}$-alkyl, very particularly preferably C$_{14}$ to C$_{22}$-alkyl, in particular C$_{18}$-n-alkyl.

The alkyl radical may be unbranched, i.e. an n-alkyl radical, or be mono- or polybranched. Preferably, the alkyl radical is unbranched.

Examples of preferred hydrophobically modified acrylic acid derivatives are decyl acrylate, lauryl acrylate, myristyl acrylate, cetyl acrylate, stearyl acrylate, oleyl acrylate, behenyl acrylate, hexacosyl acrylate, decyl methacrylate, lauryl methacrylate, myristyl methacrylate, cetyl methacrylate, stearyl methacrylate, oleyl methacrylate, behenyl methacrylate or hexacosyl methacrylate. Particular preference is given to stearyl acrylate or stearyl methacrylate, in particular stearyl methacrylate.

In the use according to the invention for improving the water resistance of a cosmetic formulation, very particular preference is given to a copolymer which comprises 65 to 75% by weight, in particular about 70% by weight, of N-vinylpyrrolidone and 25 to 35% by weight, in particular about 30% by weight, of stearyl methacrylate, and which consists to more than 95% by weight, in particular exclusively, of N-vinylpyrrolidone and stearyl methacrylate.

The K value (in accordance with Fikentscher-Cellulosechemie 1932, Vol. 13, pp. 58-64 and pp. 71-74) of the copolymers which are used in the use according to the invention for improving water resistance is usually in the range from 7 to 130, preferably in the range from 15 to 100 and in particular in the range from 20 to 80. The K value of the copolymer is determined using a solution of the copolymer in ethanol or isopropanol at 25° C. at a concentration which is in the range from 0.1 to 5% by weight depending on the K value.

The copolymers used according to the invention for improving the water resistance of a cosmetic formulation can be used in solid form, for example as powders or as flakes, or as water-based dispersion. The concentration of the water-based dispersion of the copolymer can be between 1 and 50% by weight, preferably 5 to 40% by weight, particularly preferably 15 to 30% by weight. The viscosity of the aqueous dispersion depends on the content of the copolymer.

The copolymers used according to the invention for improving the water resistance of a cosmetic formulation are usually used in such a concentration in the cosmetic formulation as is required in order to achieve the desired effect to the desired degree. Preferably, the copolymers, described in more detail above, are used in an amount of from 0.1 to 10% by weight, particularly preferably in an amount of from 0.5 to 4% by weight, in particular from 1 to 3% by weight, based on the total weight of the cosmetic formulation.

The copolymers used according to the invention for improving the water resistance of a cosmetic formulation can in practice be added at any suitable point in the preparation process of the cosmetic formulation. In the case of an emulsion, the copolymers can be added to the water phase before the emulsification step, during the emulsification or heating step, during the cooling step or after the cooling step. The copolymers, described in more detail above, are dispersible in cold water (room temperature, about 20° C.) without the introduction of further heat. Furthermore, the copolymers do not have to be neutralized and also require no other special treatment steps to achieve adequate dispersion in water or other aqueous media.

Within the context of the present invention, the degree of water resistance of a cosmetic formulation can be determined by two methods.

According to the first method (wetting), the degree of water resistance is determined in an in vitro test based on the determination of the contact angle of a water drop on a surface which has been coated with the cosmetic formulation to be investigated. This method is explained in more detail in the experimental section.

The second method of determining water resistance relates to sunscreen compositions and is carried out in accordance with the in vivo method recommended by COLIPA in "Guidelines for Evaluating Sun Product Water Resistance (December 2005)", where the ratio of the sun protection factor after the action of water relative to the sun protection factor before the action of water (SPF after/SPF before) is a measure of the water resistance of the tested sunscreen formulation.

The cosmetic formulation whose water resistance can be improved according to the present invention is preferably a formulation which can be applied to the skin, the hair, the eyelashes or the eyebrows, such as, for example, a skincare composition for the face, the hands, the feet or the body, an antiaging formulation, a sunscreen composition, an insect repellant, a hairspray, a conditioning mousse, a hair gel, a blow-drying lotion, a deodorant preparation, a lip care formulation or a make-up composition for the eyes, lips or the face.

The cosmetic formulation may be present in various forms, such as, for example, as spray, emulsion, lotion, gel, liquid, stick, wax, paste, powder or cream.

Examples of skincare compositions are moisturizing lotions and creams, protection creams against contact with chemicals or pesticides, baby creams and aftersun lotions.

Examples of make-up compositions for the eyes, lips or the face are mascara, eyebrow pencils, eyeshadows, kohl, eyeliners, lip pencils, lip contour pencils, blusher, make-ups (loose or pressed powders), primers and concealing sticks.

Examples of sunscreen compositions are sunscreen emulsions, sunscreen lotions, sunscreen creams, sunscreen emulsion sprays, aqueous sunscreen gels and sunscreen liquid sprays, where the various sunscreen compositions comprise at least one organic or inorganic UV filter such as, for example, a UV-B filter, UV-A filter or broadband filter.

The cosmetic formulation whose water resistance can be improved according to the present invention comprises, besides the copolymer improving the water resistance, further ingredients approved and customarily used in the cosmetics industry, as are described, for example, in the brochure "Kosmetika—Inhaltstoffe—Funktionen [Cosmetics—Ingredients—Functions]", which was published in a completely revised edition in 2005 by the associations IKW, FCIO and SKW. In other respects, these ingredients for cosmetic formulations are known to the person skilled in the art, such as, for example, various oils, waxes, solvents, emulsifiers, preservatives, antioxidants, vitamins, perfumes, insect repellant, dyes, pigments, humectants, fillers, thickeners, stabilizers, buffers, spreading agents, acids, bases or sun protection filters (UV filters).

Preferably, the cosmetic formulation whose water resistance can be improved according to the present invention comprises at least one water-soluble, water-insoluble or sparingly water-soluble, preferably a water-insoluble or sparingly water-soluble, active ingredient or effect substance. Examples of classes of such active ingredients or effect substances are antioxidants, vitamins, antidandruff agents, bleaches, tanning agents, cosmetic dyes, pigments and effect pigments, and also UV filters, preferably pigments and effect pigments, and also UV filters.

Nonlimiting examples of pigments and effect pigments are organic lakes, iron oxides, titanium dioxide, bismuth oxychloride, aluminum powders, mica coated with titanium dioxide or iron oxide, calcium sodium borosilicate coated with titanium dioxide or iron oxide, aluminum borosilicate coated with titanium dioxide or iron oxide, synthetic fluorophlogopites coated with titanium oxide or iron oxide, carmine, Prussian blue, chromium oxide green, ultramarine blue, manganese violet, pearl essence or mother of pearl.

Nonlimiting examples of UV filters are the following commercially available UV filters approved for cosmetic applications (according to INCI nomenclature):

PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazol, BOT), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

Thus, besides the copolymer increasing the water resistance according to the invention, a preferred cosmetic formulation in the form of a sunscreen composition comprises at least one of the aforementioned UV filters.

The UV filters are used in the cosmetic formulation usually in an amount of at least 0.05% by weight to 30% by weight, in particular up to the maximum allowable concentration for the particular UV filter permitted by the respective responsible national approval authority. Preferably, the UV filters are in each case used in an amount of from 0.5% by weight to 15% by weight, particularly preferably from 1% by weight to 12% by weight, very particularly preferably from 1.5% by weight to 10% by weight, in particular from 2% by weight to 8% by weight.

Preferably, the cosmetic formulation whose water resistance can be improved according to the present invention is a sunscreen composition or a make-up composition for the eyes, the lips or the face. Particularly preferred make-up compositions are eyeliners, lipstick or mascara. The cosmetic formulation is very particularly preferably a sunscreen composition.

Besides the copolymer increasing the water resistance, the make-up composition for the eyes, lips or the face, such as, for example, mascara, make-up, lipstick, eyeshadows, blusher, kohl, usually comprises active ingredients and effect substances which have already been mentioned above by way of example.

The sunscreen composition comprises at least one suitable UV filter, preferably at least one of the aforementioned commercially available and approved UV filters, these being UV-B filters (absorption in the range between 290 and 320 nm), UV-A filters (absorption in the range between 320 and 380 nm) or broadband filters (absorption in the range between 290 and 380 nm). Sunscreen compositions usually comprise a combination of at least two UV filters, particularly preferably a combination which absorbs both in the UV-A region and in the UV-B region. The formulation of two UV filters often has a higher sun protection factor than corresponds to the sum of the values for the sun protection factors of the two comparable formulations each having only one of the two UV filters (synergism).

Preferably, in the cosmetic formulation whose water resistance can be improved according to the present invention, UV filters are usually used in each case in an amount of from 0.1 to 15% by weight, preferably from 0.5 to 10% by weight, based on the total weight of the cosmetic formulation.

Apart from at least one UV filter and the copolymer increasing the water resistance according to the invention, the sunscreen composition comprises further cosmetic auxiliaries.

Customary cosmetic auxiliaries which may be contemplated as additives are, for example, coemulsifiers, fats and waxes, stabilizers, thickeners, biogenic active ingredients, film formers, fragrances, dyes, pearlizing agents, preservatives, pigments, electrolytes (e.g. magnesium sulfate) and pH regulators. Suitable coemulsifiers are preferably known W/O and also O/W emulsifiers, such as, for example, polyglycerol esters, sorbitan esters or partially esterified glycerides. Typical examples of fats are glycerides; waxes to be mentioned are inter alia beeswax, paraffin wax or microwaxes, if appropriate in combination with hydrophilic waxes. Stabilizers which can be used are metal salts of fatty acids, such as, for example, magnesium stearate, aluminum stearate and/or zinc stearate. Suitable thickeners are, for example, crosslinked polyacrylic acids and derivatives thereof, polysaccharides, in particular xanthan gum, guar guar, agar agar, alginates and tyloses, cellulose derivates, such as, for example, carboxymethylcellulose and hydroxyethylcellulose, and also higher molecular weight polyethylene glycol mono- and diesters of fatty acids, fatty alcohols, monoglycerides and fatty acids, polyacrylates (e.g. Luvigel® EM or Carbopol®), polyvinyl alcohol, polyvinylpyrrolidone and associative thickeners based on polyurethane (e.g. Luvigel® STAR from BASF). Biogenic active ingredients are to be understood as meaning, for example, plant extracts, protein hydrolysates and vitamin complexes. Customary film formers are, for example, hydrocolloids such as chitosan, microcrystalline chitosan or quaternized chitosan, polyvinylpyrrolidone, vinyl pyrrolidone-vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlizing agents are, for example, glycol distearic acid esters such as ethylene glycol distearate, but also fatty acids and fatty acid monoglycol esters. Dyes which can be used are the substances approved and suitable for cosmetic purposes, as are listed, for example, in the publication "Kosmetische Färbemittel [Cosmetic Colorants]" from the Dyes Commission of the German Research Society, published by Verlag Chemie, Weinheim, 1984. These dyes are usually used in concentrations of from 0.001 to 0.1% by weight, based on the total mixture.

An additional content of antioxidants is generally preferred. Thus, favorable antioxidants which may be used are all antioxidants that are customary or suitable for cosmetic and/or dermatological applications.

The antioxidants are advantageously selected from the group consisting of amino acids (e.g. glycine, histidine, tyrosine, tryptophan) and derivatives thereof, imidazoles (e.g. urocanic acid) and derivates thereof, peptides such as D,L-carnosine, D-carnosine, L-carnosine and derivatives thereof (e.g. anserine), carotenoids, carotenes (e.g. β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thiorodoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts), and also sulfoximine compounds (e.g. buthionine sulfoximines, homocysteine sulfoximines, buthionine sulfones, penta-, hexa-, heptathionine sulfoximine) in very low tolerated doses (e.g. pmol to µmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA and derivatives thereof, unsaturated fatty acids and derivatives thereof (e.g. γ-linolenic acid, linoleic acid, oleic acid), folic acid and derivatives thereof, ubichinone and ubichinol and derivatives thereof, vitamin C and derivatives thereof (e.g. ascorbyl palmitate, Mg-ascorbyl phosphate, ascorbyl acetate), tocopherol and derivatives (e.g. vitamin E acetate, tocotrienol), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaicic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), and stilbenes and derivatives thereof (e.g. stilbene oxide, trans-stilbene oxide).

Also advantageous are natural vegetable antioxidant complexes such as, for example, tea extracts, grape extracts or algae extracts, but also natural or nature-identical individual substances, such as, for example, resveratrol.

As well as protection of the cosmetic and/or dermatological product against oxidation, antioxidants can also achieve antioxidative and also antiaging effects in the human skin.

Consequently, within the context of the invention, very particular preference is given to antioxidants which penetrate into the human skin and efficiently develop their effect therein, and thus in the case of sunscreen formulations, in a certain sense synergistically to the sun protection filters, protect the skin against UV light damage, against sunburn and against reactive oxygen species and free radicals. Very particular preference is given to vitamin C and vitamin E and their derivatives.

The amount of the aforementioned antioxidants (one or more compounds) in the preparations is preferably 0.001 to 30% by weight, particularly preferably 0.05 to 20% by weight, in particular 1 to 10% by weight, based on the total weight of the preparation.

If vitamin E and/or derivatives thereof are used as antioxidant, it is advantageous to select their respective concentration from the range from 0.001 to 10% by weight, based on the total weight of the formulation.

If vitamin A and/or derivatives thereof or carotenoids are the antioxidant or the antioxidants, it is advantageous to select their respective concentration from the range from 0.001 to 10% by weight, based on the total weight of the formulation.

Customary oil components in cosmetics are, for example, paraffin oil, glyceryl stearate, isopropyl myristate, diisopropyl adipate, cetylstearyl 2-ethylhexanoate, hydrogenated polyisobutene, vaseline, caprylic acid/capric acid triglycerides, microcrystalline wax, lanolin and stearic acid. However, this list is illustrative and not exhaustive.

Nonlimiting examples of oils and solubilizers in cosmetics are the following (in accordance with INCI nomenclature):

Isosorbide Dimethylether, Benzotriazolyl Dodecyl p-Cresol, Dicaprylyl Maleate, Isodecyl oleate, Octyldodecyl Stearoyl stearate, Hexyl Laurate, Dibutyl adipate, Dicaprylyl carbonate, Coco caprylate/caprate, Dicaprylyl ether, 2-propylheptyl caprylate, Cetearyl Isononanoate, Butylene glycol cocoate, Diethylhexyl 2.6-naphthalate, Tri C12-13 alkyl citrate, C12-13 alkyl lactate, Di C12-C13 alkyl malate, C12-13 alkyl octanoate, Tridecyl salicylate, Di C12-13 alkyl tartrate, Butyl stearate, Diethylhexyl adipate, Lauryl lactate, Ethylhexyl cocoate, Ethylhexyl hydrostearate, Octyl stearate, Diethylhexyl succinate, PPG-2 Myristyl ether propionate, Pentaerythrityl tetracaprylate/caprate, Pentaerythrityl tetraisostearate, PPG-3 Benzyl Ether Myristate, Isotridecyl isononanoate, Di PPG-3 Myristyl ether adipate, Di PPG-2 Myreth-10 adipate, Cyclomethicone, N,N-diethyl-m-Toluamide, Butylene glycol dicaprylate/dicaprate, Triheptanoin, Isodecyl Isononanoate, Isocetyl salicylate, Isodecyl salicylate, Ethylhexyl Ethylhexanoate, Diisopropyl adipate, Diisopropyl sebacate, Neopentyl Glycol Diheptanoate, Isostearyl Neopentanoate, Isodecyl neopentanoate and Diisopropyl Sebacate and Lauryl Lactate, Isodecyl neopentanoate, Isopropyl Lauroyl Sarcosinate, Dipropylene glycol/dicaprate/dicaprylate, Trioctanoin, Alcohol denat., Octyldodecanol, Ethylhexyl benzoate, Octyldodecyl Benzoate, Dipropylene glycol dibenzoate, Isostearyl Benzoate, C12-15 alkyl benzoate, C12-15 alkyl benzoate & dipropylene glycol dibenzoate & PPG-15 stearyl ether benzoate, Butyloctyl Salicylate, Ethylbutylacetyl aminopropionate, Isopropyl Myristate, Isopropyl Palmitate, Jojoba oil, Isononyl Isononanoate, Neopentyl glycol diheptanoate, Propylene Glycol Dibenzoate, Polyester-10 and Propylene glycol Dibenzoate, Polyester-7 & neopenthyl glycol diheptanoate, Propylene glycol dicaprylate/dicaprate, Tridecyl Trimellitate, Decyltetradecyl Cetearate, Methylene dimethylether, Cocoglycerides, Polydecene, Butyl Ethylpropane-diyl ethylhexanoate, Octyl palmitate, Mineral Oil, Hydrogenated polyisobutene & tocopherol, Squalene, Propylene Glycol Isostearate, Isostearyl Isostearate, Octyldodecyl Lactate, Polyglyceryl-2 Triisostearate, Erythrityl Triethylhexanoate, Diisopropyl dimer dilinoleate, PEG/PPG-5/3 Trisiloxane, Diethylhexyl malate, Dimethyl capramide, Caprylyl pyrrolidone, Cetyl hexylhexanoate, Caprylic/capric triglyceride, Decyl cocoate, Diethylhexyl carbonate, Cetearyl Ethylhexanoate, Ethylhexyl stearate, Isopropyl stearate, Tris(PPG-3 Benzyl Ether) citrate, Cetyl PPG-2 isodeceth-7 carboxylate, Isopropyl PPG-2 isodeceth-7 carboxylate, Isopropyl C12-15 pareth-9 carboxylate, PPG-3 Myristylether, Phenethyl benzoate, Propylene Glycol, Vitamin E Acetate, and the UV filters liquid at room temperature Octyl dimethyl PABA, Homosalate, Octocrylene, Isoamyl p-methoxycinnamate, Octyl salicylate, Ethylhexyl Methoxycinnamate, Polysilicone-15.

Preference is given to the following oils and solubilizers (in accordance with INCI nomenclature):

Dibutyl adipate, Dicaprylyl carbonate, 2-propylheptyl caprylate, Diethylhexyl 2,6-naphthalate, C12-13 alkyl lactate, Di C12-C13 alkyl malate, Di C12-13 alkyl tartrate, PPG-2 Myristyl ether propionate, Pentaerythrityl tetrasiostearate, N,N-diethyl-m-Toluamide, Butylene glycol dicaprylate/dicaprate, Triheptanoin, Isodecyl salicylate, Diisopropyl adipate, Diisopropyl sebacate, Isodecyl neopentanoate and Diisopropyl Sebacate and Lauryl Lactate, Isodecyl neopentanoate, Isopropyl Lauroyl Sarcosinate, Propylene glycol/dicaprate/dicaprylate, Ethylhexyl benzoate, C12-15 alkyl benzoate, C12-15 alkyl benzoate & dipropylene glycol dibenzoate & PPG-15 stearyl ether benzoate, Ethylbutylacetyl aminopropionate, Isopropyl Myristate, Isopropyl Palmitate, Isononyl Isononanoate, Propylene Glycol Dibenzoate, Propylene glycol dicaprylate/dicaprate, Cocoglycerides, Caprylic/capric triglyceride, Decyl cocoate, Diethylhexyl carbonate, Isopropyl PPG-2 isodeceth-7 carboxylate, Isopropyl C12-15 pareth-9 carboxylate, Phenethyl benzoate, Propylene Glycol.

Particular preference is given to the following oils and solubilizers (in accordance with INCI nomenclature):

Dibutyl adipate, Dicaprylyl carbonate, Di C12-13 alkyl tartrate, N,N-diethyl-m-Toluamide, Butylene glycol dicaprylate/dicaprate, Triheptanoin, Ethylhexyl benzoate, C12-15 alkyl benzoate, Ethylbutylacetyl aminopropionate, Isopropyl Myristate, Isopropyl Palmitate, Diethylhexyl carbonate, Phenethyl benzoate, Propylene Glycol.

In addition, within the context of the present invention, natural and/or nature-identical and/or synthetic active substances with different active functions may be added to the preparations, such as, for example, caffeine for tightening the skin or promoting circulation, dihydroxyacetone and/or erythrulose for the purpose of self-tanning, bisabolol and/or panthenol for calming the skin and/or substances for moisture enrichment (moisturizing), for skin smoothing, and in particular active substances for protecting against skin aging, such as, for example, vitamin A and/or derivatives thereof, plant extracts or else protein-like substances.

Further components of cosmetic and/or dermatological preparations within the context of the present invention can fulfill additional functions, such as, for example, the coloring of the skin in decorative cosmetics, but also that of the product itself. Here, pigment-like, oil-soluble and/or water-soluble cosmetic color-imparting raw materials are generally used.

The total fraction of the auxiliaries and additives can be 1 to 80% by weight, preferably 6 to 40% by weight and the nonaqueous fraction ("active substance") can be 20 to 80% by weight, preferably 30 to 70% by weight—based on the cosmetic formulations. The cosmetic formulations can be produced in a manner known per se, i.e. for example by hot, cold, hot-hot/cold or PIT emulsification. This is a purely mechanical process, a chemical reaction does not take place.

The compositions obtainable by the process according to the invention are thus in particular sunscreen preparations, which may be present in liquid, pasty or solid form, for example as water-in-oil creams, oil-in-water creams or lotions, aerosol and pump foams, foam creams, gels, oils, grease sticks, powders, sprays or alcoholic-aqueous lotions.

Finally, in principle also further substances known per se which contribute to increasing water resistance may be added to the cosmetic formulation.

It has been established that the sun protection factor of a sunscreen composition is increased by adding the copolymer improving the water resistance.

Increasing the sun protection factor of a cosmetic formulation which comprises at least one UV filter by adding a substance which is not a UV filter offers the possibility of reducing the amount of UV filters in a sunscreen composition without simultaneously also lowering the UV protection performance.

The invention therefore also further provides the use of copolymers comprising
a) 40 to 95% by weight of N-vinylpyrrolidone and
b) 5 to 60% by weight of a hydrophobically modified acrylic acid derivative
as agents for improving the water resistance of a sunscreen composition which comprises at least one UV filter and/or for increasing the sun protection factor of this sunscreen composition which comprises at least one UV filter.

Preferred embodiments with regard to the copolymer and the further ingredients of a sunscreen formulation can be found in the explanations already given above.

The present invention likewise provides a method for improving the water resistance of a cosmetic formulation, where a copolymer comprising
a) 40 to 95% by weight of N-vinylpyrrolidone and
b) 5 to 60% by weight of a hydrophobically modified acrylic acid derivative
is added to the preparation of the cosmetic formulation.

Preferred embodiments with regard to the copolymer can be found in the explanations already given above. The copolymer can in practice be added at any suitable point during the preparation of the cosmetic formulation. In the case of an emulsion, the copolymers are preferably added to the water phase.

Suitable emulsions are inter alia also O/W macroemulsions, O/W microemulsions or O/W/O emulsions, the emulsions being obtainable by phase inversion technology, as in DE-A-197 26 121.

The invention also further provides a cosmetic formulation selected from the group consisting of sunscreen compositions and make-up compositions for the eyes, the lips or the face, comprising at least one water-insoluble or sparingly water-soluble active ingredient or effect substance and at least one copolymer comprising
a) 40 to 95% by weight of N-vinylpyrrolidone and
b) 5 to 60% by weight of a hydrophobically modified acrylic acid derivative.

Preferred embodiments as regards the copolymer can be found in the explanations already given above.

The invention also likewise provides a sunscreen formulation comprising at least one UV filter and at least one copolymer comprising
a) 40 to 95% by weight of N-vinylpyrrolidone and
b) 5 to 60% by weight of a hydrophobically modified acrylic acid derivative.

Preferred embodiments as regards the copolymer can be found in the explanations already given above. Possible further ingredients and formulation types have already been discussed in the discussion of the sunscreen composition.

The invention also further provides a make-up composition for the eyes, the lips or the face, comprising at least one dye, one pigment or one effect pigment and at least one copolymer comprising
a) 40 to 95% by weight of N-vinylpyrrolidone and
b) 5 to 60% by weight of a hydrophobically modified acrylic acid derivative.

Preferred embodiments as regards the copolymer can be found in the explanations already given above.

The cosmetic formulations may be transparent or nontransparent and be present in the following types or forms: lotions, milk, cream, spray, shake-well, foam, gel, cream gel, water-containing gel, oil-in-water emulsion, water-in-oil emulsion, oil-in-water-in-oil emulsion, water-in-oil-in-water emulsion, water/silicone emulsion, silicone/water emulsion, hydro-alcohol solution, alcohol solution, silicone gel, single-phase oil formulation, pressed or loose powder, lipstick, surfactant-free gel.

Preferably, the copolymer, both in the cosmetic formulation selected from the group consisting of sunscreen composition and make-up composition for the eyes, the lips or the face, comprising at least one water-insoluble or sparingly water-soluble active ingredient or effect substance, and also in the sunscreen formulation comprising at least one UV filter, and also in the make-up composition for the eyes, the lips or the face comprising at least one dye, one pigment or one effect pigment, comprises
a) 60 to 80% by weight of N-vinylpyrrolidone and
b) 20 to 40% by weight of the hydrophobically modified acrylic acid derivative,
where the hydrophobically modified acrylic acid derivative is an acrylic acid ester or methacrylic acid ester of the formula I,

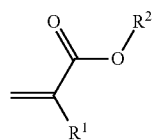

(I)

in which
$R^1$ is hydrogen or methyl, in particular methyl and
$R^2$ is $C_8$ to $C_{32}$-alkyl, preferably $C_{10}$ to C28-alkyl, particularly preferably $C_{12}$ to $C_{24}$-alkyl, very particularly preferably $C_{14}$ to $C_{22}$-alkyl, in particular $C_{18}$-n-alkyl,
and
where the copolymer consists to more than 90% by weight, in particular to more than 95% by weight, of N-vinylpyrrolidone and the hydrophobically modified acrylic acid derivative.

Very particularly preferably, the cosmetic formulation modified to be water-resistant or the sunscreen formulation modified to be water-resistant or the make-up composition for the eyes, the lips or the face comprises a copolymer which comprises 65 to 75% by weight, in particular about 70% by weight, of N-vinylpyrrolidone and 25 to 35% by weight, in particular about 30% by weight, of stearyl methacrylate, and which consists to more than 95% by weight, in particular exclusively, of N-vinylpyrrolidone and stearyl methacrylate.

Preferably, the sunscreen formulation modified to be water-resistant comprises at least one UV filter selected from the group consisting of
PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxyphenol Methoxyphenyl Triazine (AT), Polysilicone 15, Diethylamino Hydroxybenzoyl Hexyl Benzoate, 2,4,6-Tris (biphenyl)-1,3,5-triazine (TBT), Methanone 1,1'-(1,4-piperazinediyl)bis[1-[2-[4-(diethylamino)-2-hydroxybenzoyl]phenyl]] (CAS number 919803-06-8), 1,1-Di-(carboxy-(2',2'-dimethyl-propyl))-4,4-diphenylbutadiene, Merocyanine derivatives, Benzylidene Malonate UVB filters, Titanium Dioxide and Zinc Oxide.

The sunscreen formulation modified to be water-resistant particularly preferably comprises at least one UV filter selected from the group consisting of:
Homomenthyl Salicylate (HMS), Phenylbenzimidazole Sulfonic Acid (PBSA), Butyl Methoxydibenzoylmethane (BMDBM), Octocrylene (OC), Ethylhexyl Methoxycinnamate (EMC), Ethylhexyl Triazone (OT, ET), Diethylhexyl Butamido Triazone (DBT), Ethylhexyl Salicylate (OS, ES), Methylene Bis-Benzotriazolyl Tetramethylbutylphenol (Bisoctyltriazole, BOT), Bis-Ethylhexyloxyphenol Methoxyphenyl Triazine (AT), Diethylamino Hydroxybenzoyl Hexyl Benzoate (DHHB), 2,4,6-Tris (biphenyl)-1,3,5-triazine (TBT), Methanone 1,1'-(1,4-piperazinediyl)bis[1-[2-[4-(diethylamino)-2-hydroxybenzoyl]phenyl]] (CAS number 919803-06-8), Merocyanine derivatives, Benzylidene Malonate UVB filters and Titanium Dioxide.

The merocyanine derivates are described in WO 2004006878, particular preference being given to the formula (A) or (B), which may both be present in their E or Z configurations.

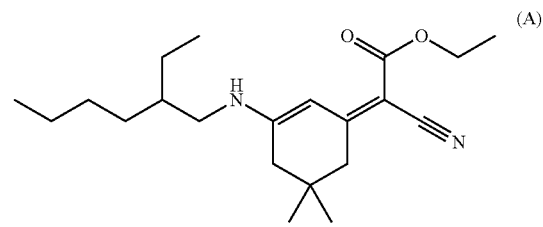

(A)

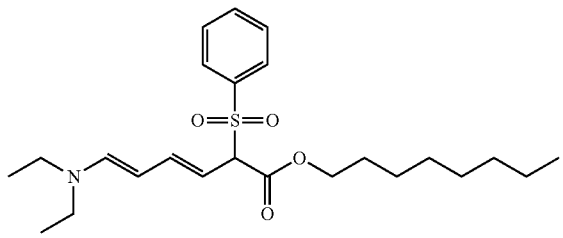

(B)

The benzylidene malonate UVB filters preferably correspond to the formula (C) or (D).

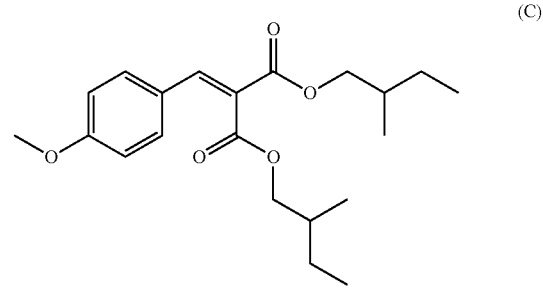

(C)

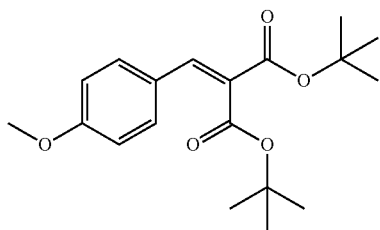
(D)

Particular preference is given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter ethylhexyltriazone (OT, ET) comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxy-cinnamate (IMC), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Homosalate (HMS), comprise at least a second UV filter selected from the group consisting of PABA, Camphor Benzalkonium Methosulfate, Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxy-phenol Methoxyphenyl Triazine (AT), Polysilicone 15,Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Phenylbenzimidazole Sulfonic Acid (PBSA), comprise at least a second UV filter selected from the group consisting of PABA, Camphor Benzalkonium Methosulfate, Homosalate (HMS), Benzophenone-3 (BENZ-3), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Butyl Methoxydibenzoylmethane (BMDBM), comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Octocrylene (OC), comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Ethylhexyl Methoxycinnamate (EMC, OMC), comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Ethylhexyl Salicylate (OS, ES), comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (I MC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Methylene Bis-Benzotriazolyl Tetramethylbutylphenol (Bisoctyltriazole, BOT), comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and), Bis-Ethylhexyloxyphenol Methoxyphenyl Triazine (AT), comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BIPolysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Diethylamino Hydroxybenzoyl Hexyl Benzoate, comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxy-phenol Methoxyphenyl Triazine (AT), Polysilicone 15, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter 2,4,6-tris (biphenyl)-1,3,5-triazine (TBT), comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxy-phenol Methoxyphenyl Triazine (AT), Polysilicone 15, Diethylamino Hydroxybenzoyl Hexyl Benzoate, Titanium Dioxide and Zinc Oxide.

Particular preference is likewise given to sunscreen formulations modified to be water-resistant which, besides the copolymer increasing the water resistance, in particular the copolymer comprising about 70% by weight of N-vinylpyrrolidone and about 30% by weight of stearyl methacrylate, and the UV filter Methanone 1,1'-(1,4-piperazinediyl)bis[1-[2-[4-(diethylamino)-2-hydroxybenzoyl]phenyl]] (CAS number 919803-06-8), comprise at least a second UV filter selected from the group consisting of PABA, Camphor Benzalkonium Methosulfate, Homosalate (HMS), Benzophenone-3 (BENZ-3), Phenylbenzimidazole Sulfonic Acid (PBSA), Terephthalidene Dicamphor Sulfonic Acid, Butyl Methoxydibenzoylmethane (BMDBM), Benzylidene Camphor Sulfonic Acid, Octocrylene (OC), Polyacrylamidomethyl Benzylidene Camphor, Ethylhexyl Methoxycinnamate (EMC, OMC), PEG-25 PABA (PEG-PABA), Isoamyl p-Methoxycinnamate (IMC), Ethylhexyl Triazone (OT, ET), Drometrizole Trisiloxane, Diethylhexyl Butamido Triazone (DBT), 4-Methylbenzylidene Camphor (MBC), 3-Benzylidene Camphor (BC), Ethylhexyl Salicylate (OS, ES), Ethylhexyl Dimethyl PABA (OD-PABA, ED-PABA), Benzophenone-4 (BENZ-4), Methylene Bis-Benzotriazolyl Tetramethylbutylphenol (Bisoctyltriazole, BOT), Bisimidazylate (BI), Bis-Ethylhexyloxyphenol Methoxyphenyl Triazine (AT), Polysilicone 15, Diethylamino Hydroxybenzoyl Hexyl Benzoate, Titanium Dioxide and Zinc Oxide.

The use according to the invention of the copolymers described above which comprise N-vinylpyrrolidone and a hydrophobically modified acrylic acid derivative as agents for improving the water resistance of a cosmetic formulation leads to cosmetic formulations with excellent water resistance which do not leave behind a waxy, greasy or oily impression when applied to the skin. The copolymers used in the use according to the invention can be incorporated without problems during the preparation of the cosmetic formulation either into the aqueous phase or into the oil phase. Incorporation of the copolymer in powder form into a mixture of solids is also possible.

Furthermore, the use according to the invention of the copolymers described above leads in the case of sunscreen compositions which comprise at least one UV filter, besides or else independently of increased water resistance, to an increase in the sun protection factor.

The cosmetic formulations according to the invention which comprise the above-described copolymer of N-vinylpyrrolidone and a hydrophobically modified acrylic acid derivative are characterized by excellent water resistance without leaving behind a waxy, greasy or oily impression when applied to the skin.

The invention is illustrated by the following examples, although these do not limit the invention:

EXAMPLES

Example 1

Preparation of a Water-resistant Sunscreen Formulation

| Phase | Product | INCI Name | V1 | V2 | B1 |
|---|---|---|---|---|---|
| Phase A | Cremophor A 6 | Ceteareth-6, Stearyl Alcohol | 3.5 | 3.5 | 3.5 |
| | Cremophor A 25 | Ceteareth-25 | 1.5 | 1.5 | 1.5 |
| | Lanette O | Cetearyl Alcohol | 1.0 | 1.0 | 1.0 |
| | Uvinul ® A Plus | Diethylamino Hydroxybenzoyl Hexyl Benzoate | 5.0 | 5.0 | 5.0 |
| | Uvinul ® N 539 | Octocrylene | 10.0 | 10.0 | 10.0 |
| | Cetiol B | Dibutyl Adipate | 5.0 | 5.0 | 5.0 |
| | Antaron V 220 | VP/Eicosene Copolymer | | 2.0 | |
| Phase B | Keltrol CG-T | Xanthan Gum | 0.5 | 0.5 | 0.5 |
| | Copolymer 1 | | | | 2.0 |
| | Water | Aqua | ad 100 | ad 100 | ad 100 |
| Phase C | Euxyl K 300 | Phenoxyethanol, Methylparaben, Butylparaben, Ethylparaben, Propylparaben, Isobutylparaben | 0.3 | 0.3 | 0.3 |

Antaron V 220, known in the USA as Ganex V 220, is a long-chain alpha-olefin/vinylpyrrolidone copolymer from ISP.

Copolymer 1 is a copolymer which comprises ca. 70% by weight of N-vinylpyrrolidone and ca. 30% by weight of stearyl methacrylate, and which consists to more than 99% by weight of N-vinylpyrrolidone and stearyl methacrylate. Copolymer 1 is prepared in accordance with the process described in example 5 of EP patent 1 669 374 A1 firstly in the form of an aqueous dispersion, and is then obtained as a dry and pourable powder as a result of spray-drying as in the example of EP patent 1 669 374 A1. Copolymer 1 has a K value (1% strength in ethanol) of 45.1, which corresponds to a molecular weight of ca. 136000 g/mol.

Preparation:
Phase A and phase B were heated separately to ca. 85° C.
Phase B was stirred into phase A, and the mixture A+B was homogenized.
The mixture A+B was cooled to ca. 30° C. with stirring.
Phase C was stirred into the mixture A+B, and the mixture was homogenized and then cooled to room temperature with stirring.

Example 2

Determination of the in vivo SPF Values in Accordance with COLIPA

The SPF in vivo values were determined by an external institute in accordance with the guidelines recommended by COLIPA "International Sun Protection Factor (SPF) Test Method" (May 2006).

| Formulation | SPF in vivo (ProDerm) |
|---|---|
| V1 | 8.1 |
| V2 | 8.5 |
| B1 | 10.7 |

SPF in vivo (ProDerm): SPF in vivo values which were measured according to COLIPA's in vivo measurement method by proDERM Institute for Applied Dermatological Research GmbH.

The in vivo SPF values measured by the independent institute show that example B1 according to the invention has a considerably higher in vivo SPF value compared to the two comparative examples V1 (no additional polymer for increasing the water resistance) and V2 (Antaron V 220 as additional polymer for increasing the water resistance). This means that the addition of copolymer 1 leads to an increase in the sun protection factor.

Example 3

Determination of the Water Resistance in Accordance with the COLIPA in vivo "Very Water Resistant" Test Method The "Very Water Resistant" values were measured in accordance with the in vivo method recommended by COLIPA in "Guidelines for Evaluating Sun Product Water Resistance (December 2005)":

| Formulation | Very Water Resistant values [%] |
|---|---|
| V1 | 21.0 |
| V2 | 59.7 |
| B1 | 57.9 |

The "Very Water Resistant" value for formulation V1 is significantly less than 50%, which, according to the COLIPA method, means that the formulation is not "very water resistant".

The "Very Water Resistant" values for formulations V2 and B1 are very similar and are significantly higher than 50%, which indicates that both formulations have similar water resistance and, according to the COLIPA method, both formulations are "very water resistant".

The in vivo "Very Water Resistant" test shows here that both polymers, Antaron V220 and copolymer 1, increase the water resistance of a sunscreen formulation in such a way that both formulations can be referred to as "very water resistant".

Example 4

Determination of the Water Resistance According to the in vitro Contact Angle Measurement on MMA Plates Method Description:

The substrate used is roughened polymethyl methacrylate (PMMA) plates, as recommended in the "In Vitro UVA Method" published by COLIPA in 2007 and updated in 2009. These PMMA plates are produced and sold by Schönberg GmbH & Co. KG (Germany). The defined roughness is produced by means of sandblasting in a water fluidizing method. The plates with a roughness of 2 μm are used for the method described below.

The formulation to be tested is applied to the PMMA plates in accordance with the same principle as described in the "In Vitro UVA Method" published by COLIPA in 2007 and updated in 2009. The amount to be applied per PMMA plate is 1.00 mg/cm². A triple determination is carried out per formulation, i.e. the same formulation is applied to three plates. After the initial weighing, using the index finger, which is covered with a single-use fingerstall made of latex and saturated beforehand with the formulation, the formulation is spread evenly on the plate and rubbed in using small circular movements. It is important that the corners are also filled. As soon as the emulsion "breaks" (becomes clear), the plate is also treated with a slight pressure and horizontal streaking movements. After this procedure, the plates are stored at room temperature in a cardboard box in the dark for 30 minutes. Measurement of the plate then takes place.

The contact angle is measured manually using the contact angle measuring device easy drop from Krüss GmbH Hamburg, Germany and the associated software DSA1. The precision dosing needles with polypropylene tubes Art. 5125PPS-B, with an internal diameter of 0.48 mm and external diameter of 0.86 mm from GLT Gesellschaft für Löttechnik mbH Pforzheim, Germany are screwed onto a 2 ml syringe. The cylinder of the syringe is removed and its plunger placed on the rotatable stainless steel cylinder. This device is placed on the syringe in order to be able to better dose the amount of water.

For the dripping, double distilled water with an insulation resistance of 18.2 MOhm×cm is used.

30 water drops are applied to each plate. Each drop is measured immediately after application and adjustment of the baseline for exactly 5 seconds. Here, an image is recorded every 0.5 seconds. To evaluate the drop contour by means of the software DSA1, tangent method 1 is exclusively used (see the website http://www.kruss.de/de/theorie/messungen/kontaktwinkel/messung-des-kontaktwinkels.html). Per drop, ca. 10 images are recorded during the 5 s measurement and therefore ca. 10 contact angles are measured. An average is calculated from these by the software.

The 30 drops per plate then give rise to 30 contact angles, from which an average is calculated. The contact angle of the formulation is the average calculated from the three plates.

The measured contact angle allows a statement to be made about the hydrophobic property of a formulation. The higher the contact angle, the more hydrophobic the formulation. And the more hydrophobic a formulation, the more water-repellant and water-resistant it is.

| Formulation | Contact angle on PMMA plate [°] |
|---|---|
| V1 | 18 |
| V2 | 80.5 |
| B1 | 91.8 |

The results of the contact angle measurement method indicate here that formulation V1 has a very small contact angle. Formulations V2 and B1 have significantly larger contact angles. B1 containing copolymer 1 has an even larger contact angle than V2 containing Antaron V220.

Example 5

Preparation of a Water-resistant Sunscreen Formulation with SPF 7

| Phase | Product | INCI Name | V3 | V4 | B2 |
|---|---|---|---|---|---|
| Phase A | Cremophor A 25 | Ceteareth-25 | 0.35 | 0.35 | 0.35 |
| | Brij 72 | Steareth-2 | 0.65 | 0.65 | 0.65 |
| | Amphisol K | Potassium Cetyl Phosphate | 0.50 | 0.50 | 0.50 |
| | Lanette 16 | Cetyl Alcohol | 1.00 | 1.00 | 1.00 |
| | Lanette 22 | Behenyl Alcohol | 0.75 | 0.75 | 0.75 |
| | Uvinul ® MC 80 | Ethylhexyl Methoxycinnamate | 5.00 | 5.00 | 5.00 |
| | Isohexadecane | Isohexadecane | 4.00 | 4.00 | 4.00 |
| | Abil 350 | Dimethicone | 1.00 | 1.00 | 1.00 |
| | Antaron V 216 | VP/Hexadecene Copolymer | | 2.00 | |
| | Copolymer 1 | | | | 2.00 |
| Phase B | Water | Aqua demin. | ad 100 | ad 100 | ad 100 |
| | Glycerol | Glycerin | 3.00 | 3.00 | 3.00 |
| | Edeta BD | Disodium EDTA | 0.05 | 0.05 | 0.05 |
| | Keltrol | Xanthan Gum | 0.30 | 0.30 | 0.30 |
| | Carbopol Ultrz 10 P | Carbomer | 0.30 | 0.30 | 0.30 |
| | Triethanolamine Care | Triethanolamine | 0.06 | 0.06 | 0.06 |
| Phase C | Euxyl K 300 | Phenoxyethanol, Methylparaben, Butylparaben, Ethylparaben, Propylparaben, Isobutylparaben | 0.50 | 0.50 | 0.50 |

Preparation:
Phase A and phase B were heated separately to ca. 85° C.
Phase B was stirred into phase A, and the mixture A+B was homogenized.
The mixture A+B was cooled to ca. 30° C. with stirring.
Phase C was stirred into the mixture A+B, and the mixture was homogenized and then cooled to room temperature with stirring.

Example 6

Determination of the Water Resistance According to the in vitro Contact Angle Measurement on PMMA Plates in Accordance with the Measurement Method Described in Example 4.

| Formulation | Contact angle on PMMA plate [°] |
|---|---|
| V3 | 15.3 |
| V4 | 36.5 |
| B2 | 120.7 |

The results of the contact angle measurement method indicate here that formulation V3 has a very small contact angle. The contact angle of formulation V4 is slightly larger than the contact angle of formulation V3, although the contact angle remains moderate. Formulation B2 has a significantly larger contact angle than formulations V3 and V4. Formulation B2 containing copolymer 1 has a much larger contact angle than V4 containing Antaron V216.

Example 7

Preparation of a Water-resistant Sunscreen Formulation with SPF 14

| Phase | Product | INCI Name | V5 | V6 | V7 | V8 |
|---|---|---|---|---|---|---|
| Phase A | Cremophor A 6 | Ceteareth-6, Stearyl Alcohol | 3.5 | 3.5 | 3.5 | 3.5 |
| | Cremophor A 25 | Ceteareth-25 | 1.5 | 1.5 | 1.5 | 1.5 |
| | Lanette O | Cetearyl Alcohol | 1.0 | 1.0 | 1.0 | 1.0 |
| | Uvinul ® A Plus | Diethylamino Hydroxybenzoyl Hexyl Benzoate | 5.0 | 5.0 | 5.0 | 5.0 |
| | Uvinul ® N 539 | Octocrylene | 10.0 | 10.0 | 10.0 | 10.0 |
| | Cetiol B | Dibutyl Adipate | 5.0 | 5.0 | 5.0 | 5.0 |
| | Antaron V 220 | VP/Eicosene Copolymer | | 2.0 | | |

-continued

| Phase | Product | INCI Name | V5 | V6 | V7 | V8 |
|---|---|---|---|---|---|---|
| | Lexfilm Sun | Polyester-7, Neopentyl Glycol Diheptanoate | | | 2.0 | |
| | Soltex OPT (48% act. content) | Acrylates/C12-22 Alkyl Methacrylate Copolymer | | | | 4.0 |
| | Copolymer 1 | | | | | |
| Phase B | Keltrol CG-T | Xanthan Gum | 0.5 | 0.5 | 0.5 | 0.5 |
| | NaOH 10% | | | | | 5.4 |
| | Water | Aqua | ad 100 | ad 100 | ad 100 | ad 100 |
| | Copolymer 1 | | | | | |
| | Copolymer 2 | | | | | |
| Phase C | Euxyl K 300 | Phenoxyethanol, Methylparaben, Butylparaben, Ethylparaben, Propylparaben, Isobutylparaben | 0.3 | 0.3 | 0.30 | 0.3 |

| Phase | Ingredient | INCI Name | B3 | B4 | B5 |
|---|---|---|---|---|---|
| Phase A | Cremophor A 6 | Ceteareth-6, Stearyl Alcohol | 3.5 | 3.5 | 3.5 |
| | Cremophor A 25 | Ceteareth-25 | 1.5 | 1.5 | 1.5 |
| | Lanette O | Cetearyl Alcohol | 1.0 | 1.0 | 1.0 |
| | Uvinul ® A Plus | Diethylamino Hydroxybenzoyl Hexyl Benzoate | 5.0 | 5.0 | 5.0 |
| | Uvinul ® N 539 | Octocrylene | 10.0 | 10.0 | 10.0 |
| | Cetiol B | Dibutyl Adipate | 5.0 | 5.0 | 5.0 |
| | Antaron V 220 | VP/Eicosene Copolymer | | | |
| | Lexfilm Sun | Polyester-7, Neopentyl Glycol Diheptanoate | | | |
| | Soltex OPT (48% act. content) | Acrylates/C12-22 Alkyl Methacrylate Copolymer | | | |
| | Copolymer 1 | | | 2.0 | |
| | Copolymer 2 | | | | 2.0 |
| Phase B | Keltrol CG-T | Xanthan Gum | 0.5 | 0.5 | 0.5 |
| | NaOH 10% | | | | 5.4 |
| | Water | Aqua | ad 100 | ad 100 | ad 100 |
| | Copolymer 1 | | 2.0 | | |
| Phase C | Euxyl K 300 | Phenoxyethanol, Methylparaben, Butylparaben, Ethylparaben, Propylparaben, Isobutylparaben | 0.3 | 0.3 | 0.3 |

Lexfilm Sun is a product from Inolex Chemical Company.

Soltex OPT is a 48% strength dispersion of an acrylate tetrapolymer from Dow Advanced Materials.

As in the case of copolymer 1, copolymer 2 is likewise a copolymer which comprises 70% by weight of N-vinylpyrrolidone and 30% by weight of stearyl methacrylate and consists to more than 99% by weight of N-vinylpyrrolidone and stearyl methacrylate.

Copolymer 2 is in principle prepared by the same process as copolymer 1, except a lower molar mass was established.

Copolymer 2 has a K value (1% strength in ethanol) of 24.8.

Preparation:

Phase A and phase B were heated separately to ca. 85° C.

Phase B was stirred into phase A, and the mixture A+B was homogenized.

The mixture A+B was cooled to ca. 30° C. with stirring.

Phase C was stirred into the mixture A+B, and the mixture was homogenized and then cooled to room temperature with stirring.

Example 8

Determination of the Water Resistance According to the in vitro Contact Angle Measurement on Pmma Plates in Accordance with the Measurement Method Described in Example 4.

| Formulation | Contact angle on PMMA plate [°] |
|---|---|
| V5 | 18.0 |
| V6 | 80.5 |
| V7 | <15 |
| V8 | <15 |

-continued

| Formulation | Contact angle on PMMA plate [°] |
|---|---|
| B3 | 91.8 |
| B4 | 91.8 |
| B5 | 92.5 |

The results of the contact angle measurement method indicate here that formulation V5 has a very small contact angle. Formulations V7 and V8 have such small contact angles that these are below the measurable limit. Formulations V6, B3, B4 and B5 have considerably larger contact angles than formulations V5, V7 and V8.

Formulation V7 containing Lexfilm Sun and formulation V8 containing Soltex OPT exhibit smaller contact angles than the placebo V5 without polymer. In these examples, both polymers Lexfilm Sun and Soltex OPT appear in each case to reduce the water resistance of the formulation.

Formulations B3 and B4 have exactly the same contact angle, which indicates that copolymer 1 can be incorporated without a discernible difference either firstly in the oil phase as well as firstly in the water phase in order to increase the water resistance of a formulation.

The contact angles of formulation B3 containing copolymer 1 and of formulation B5 containing copolymer 2 are very similar, and both contact angles are larger than the contact angle of formulation V6 containing Antaron V220. Copolymer 1 with a K value (1% strength in ethanol) of 45.1 and copolymer 2 with a K value (1% strength in ethanol) of 24.8 exhibit here a better performance in increasing the water resistance than Antaron V220.

Example 9

Preparation of a Water-resistant Sunscreen Formulation Containing Titanium Dioxide with SPF 18

| Phase | Product | INCI Name | V9 | V10 | B6 |
|---|---|---|---|---|---|
| Phase A | Cremophor A 6 | Ceteareth-6, Stearyl Alcohol | 3.5 | 3.5 | 3.5 |
| | Cremophor A 25 | Ceteareth-25 | 1.5 | 1.5 | 1.5 |
| | Lanette O | Cetearyl Alcohol | 1.0 | 1.0 | 1.0 |
| | Uvinul ® A Plus | Diethylamino Hydroxybenzoyl Hexyl Benzoate | 5.0 | 5.0 | 5.0 |
| | Uvinul ® N 539 | Octocrylene | 10.0 | 10.0 | 10.0 |
| | Cetiol B | Dibutyl Adipate | 5.0 | 5.0 | 5.0 |
| | Antaron V 220 | VP/Eicosene Copolymer | | 2.0 | |
| Phase B | T-Lite SF-S | Titanium Dioxide, Hydrated Silica, Hydrogen Dimethicone, Aluminum Hydroxide | 2.5 | 2.5 | 2.5 |
| Phase C | Keltrol CG-T | | | 0.5 | 0.5 |
| | Water | Aqua | ad 100 | ad 100 | ad 100 |
| | Copolymer 1 | | | | 2.0 |
| Phase D | Euxyl K 300 | Phenoxyethanol, Methylparaben, Butylparaben, Ethylparaben, Propylparaben, Isobutylparaben | 0.3 | 0.3 | 0.3 |

Preparation:

Phase A was heated to 85° C., and after phase A had completely melted, phase B was added. The mixture A+B was homogenized. Phase C was heated to ca. 85° C., briefly homogenized, and then homogenized into the mixture A+B. The mixture A+B+C was stirred under cold conditions. At ca. 30° C., phase D was added. Then, the mixture A+B+C+D was afterhomogenized and cooled to room temperature with stirring.

Example 10

Determination of the Water Resistance According to the in vitro Contact Angle Measurement on Pmma Plates in Accordance with the Measurement Method Described in Example 4.

| Formulation | Contact angle on PMMA plate [°] |
|---|---|
| V9 | 28.1 |
| V10 | 55.1 |
| B6 | 56.4 |

The results of the contact angle measurement method indicate here that formulation V9 has a small contact angle and formulations V10 and B6 have larger contact angles. Formulation B6 containing copolymer 1 is at least as water-resistant as formulation V10 containing Antaron V220.

Example 11

Preparation of a Water-resistant Sunscreen Formulation Containing Zinc Oxide with SPF 16

| Phase | Product | INCI Name | V11 | V12 | B7 |
|---|---|---|---|---|---|
| Phase A | Cremophor A 6 | Ceteareth-6, Stearyl Alcohol | 3.5 | 3.5 | 3.5 |
| | Cremophor A 25 | Ceteareth-25 | 1.5 | 1.5 | 1.5 |
| | Lanette O | Cetearyl Alcohol | 1.0 | 1.0 | 1.0 |
| | Uvinul ® A Plus | Diethylamino Hydroxybenzoyl Hexyl Benzoate | 5.0 | 5.0 | 5.0 |
| | Uvinul ® N 539 | Octocrylene | 10.0 | 10.0 | 10.0 |
| | Cetiol B | Dibutyl Adipate | 5.0 | 5.0 | 5.0 |
| | Antaron V 220 | VP/Eicosene Copolymer | | 2.0 | |
| Phase B | Z-Cote HP1 | Zinc Oxide, Triethoxycaprylylsilane | 2.0 | 2.0 | 2.0 |
| Phase C | Keltrol CG-T | | | 0.5 | 0.5 |
| | Water | Aqua | ad 100 | ad 100 | ad 100 |
| | Copolymer 1 | | | | 2.0 |
| Phase D | Euxyl K 300 | Phenoxyethanol, Methylparaben, Butylparaben, Ethylparaben, Propylparaben, Isobutylparaben | 0.3 | 0.3 | 0.3 |

Preparation:

Phase A was heated to 85° C., and after phase A had completely melted, phase B was added. The mixture A+B was homogenized. Phase C was heated to ca. 85° C., briefly homogenized, and then homogenized into the mixture A+B. The mixture A+B+C was stirred under cold conditions. At ca. 30° C., phase D was added. The mixture A+B+C+D was then afterhomogenized and cooled to room temperature with stirring.

Example 12

Determination of the Water Resistance According to the in vitro Contact Angle Measurement on Pmma Plates in Accordance with the Measurement Method Described in Example 4.

| Formulation | Contact angle on a PMMA plate [°] |
|---|---|
| V11 | 35.9 |
| V12 | 75.2 |
| B7 | 87.8 |

The results of the contact angle measurement method indicate here that formulation V11 has a moderate contact angle and formulations V12 and B7 have considerably larger contact angles. Formulation B7 containing copolymer 1 has a still larger contact angle than formulation V12 containing Antaron V220 and is therefore yet more water-resistant.

Example 13

Preparation of a Water-resistant Sunscreen Formulation with SPF 30

| Phase | Product | INCI Name | V13 | V14 | B8 |
|---|---|---|---|---|---|
| Phase A | Finsolv TN | C12-15 Alkyl Benzoate | 6.5 | 6.5 | 6.5 |
| | Eutanol G | Octyldodecanol | 4.5 | 4.5 | 4.5 |
| | Parsol 1789 | Butyl Methoxydibenzoylmethane | 4.5 | 4.5 | 4.5 |
| | Uvinul ® N 539 T | Octocrylene | 4.0 | 4.0 | 4.0 |
| | Lanette 16 | Cetyl Alcohol | 3.0 | 3.0 | 3.0 |
| | Tinosorb S | Bis-Ethylhexyloxyphenol Methoxyphenyl Triazine | 2.5 | 2.5 | 2.5 |
| | Lanette O | Cetearyl Alcohol | 1.5 | 1.5 | 1.5 |
| | Cetiol MM | Myristyl Myristate | 2.0 | 2.0 | 2.0 |
| | Imwitor 960K | Glyceryl Stearate SE | 2.0 | 2.0 | 2.0 |
| | Dry Flo | | 1.0 | 1.0 | 1.0 |
| | Antaron V 220 | | | 2.0 | |
| | Cremophor CO 40 | PEG 40 Hydrogenated Castor Oil | 1.0 | 1.0 | 1.0 |

-continued

| Phase | Product | INCI Name | V13 | V14 | B8 |
|---|---|---|---|---|---|
| Phase B | T-Lite SF | Titanium Dioxide, Aluminum Hydroxide, Dimethicone/Methicone Copolymer | 1.0 | 1.0 | 1.0 |
| Phase C | Water | | | | |
| | Eusolex 232 | Phenylbenzimidazole Sulfonic Acid | 3.0 | 3.0 | 3.0 |
| | Triethanolamine | Triethanolamine | 2.0 | 2.0 | 2.0 |
| | Trilon BD | Disodium EDTA | 0.1 | 0.1 | 0.1 |
| | Glycerol | Glycerin | 6.0 | 6.0 | 6.0 |
| | Keltrol T | Xanthan gum | 0.3 | 0.3 | 0.3 |
| | Copolymer 1 | | | | 2.0 |
| Phase D | Ethanol | Alcohol | 10.0 | 10.0 | 10.0 |
| | Vitamin E acetate | Tocopheryl Acetate | 1.0 | 1.0 | 1.0 |
| | Euxyl PE 9010 | Phenoxyethanol, Ethylhexylglycerin | 1.0 | 1.0 | 1.0 |

Preparation:

Phase A was heated to 85° C., and after phase A had completely melted, phase B was added. The mixture A+B was homogenized. Phase C was heated to ca. 85° C., briefly homogenized, and then homogenized into the mixture A+B. The mixture A+B+C was stirred under cold conditions. At ca. 30° C., phase D was added. Then, the mixture A+B+C+D was afterhomogenized and cooled to room temperature with stirring.

Example 14

Determination of the Water Resistance According to the in vitro Contact Angle Measurement on Pmma Plates in Accordance with the Measurement Method Described in Example 4.

| Formulation | Contact angle on PMMA plate [°] |
|---|---|
| V13 | 33.8 |
| V14 | 40.2 |
| B8 | 69.5 |

The results of the contact angle measurement method indicate here that formulations V13 and V14 have moderate contact angles. The contact angle of V14 is a little better than the contact angle of V13, but not as high as the contact angle of formulation B8. Formulation B8 containing copolymer 1 is significantly more water-resistant than the placebo (formulation V13) and formulation V14 containing Antaron V220.

Example 15

Preparation of a Water-resistant Eyeliner

| Phases | Product | INCI | V15 | V16 | B9 |
|---|---|---|---|---|---|
| A | Water | Aqua dem. | 62.30 | 67.30 | 65.30 |
| | Veegum Ultra | Mg—Al Silicate | 0.30 | 0.30 | 0.30 |
| | Blanose | Cellulose Gum | 0.30 | 0.30 | 0.30 |
| | Luviset Shape | Polyacrylate-22 | 5.00 | | |
| | Propylene Glycol | Propylene Glycol | 4.00 | 4.00 | 4.00 |
| | Keltrol E | Xanthan Gum | 0.65 | 0.65 | 0.65 |
| | Vilvanolin P | Isopropyl Lanolate | 2.00 | 2.00 | 2.00 |
| B | Tego Care 450 | Polyglyceryl-3-Methyl-Glucose Distearate | 1.70 | 1.70 | 1.70 |
| | DC 245 Fluid | Cyclopentasiloxane | 1.00 | 1.00 | 1.00 |
| | Dispersion of Sicovit Black in Castor Oil | | 2.00 | 2.00 | 2.00 |
| D | Reflecks ™ pigments | | 5.00 | 5.00 | 5.00 |
| C | Ethanol | Alcohol | 15.00 | 15.00 | |
| | Euxyl PE 9010 | Phenoxyethanol, Ethylhexylglycerin | 0.75 | 0.75 | |
| F | Ethanol | Alcohol | | | 15.00 |
| | Copolymer 1 | | | | 2.00 |
| | Euxyl PE 9010 | Phenoxyethanol, Ethylhexylglycerin | | | 0.75 |

The Reflecks™ pigments used in phase D are Reflecks™ Dimensions Luminous Red.

Preparation of formulations V15 and V16:

Phases A and B were each heated separately to 80° C. Phase A was added to phase B with stirring using an homogenizer (2 min at 8000-9000 rpm). The mixture A+B was then stirred under cold conditions. Below 40° C., phase C was stirred in using the homogenizer (1 min at 9000 rpm). Finally, the pigments (phase D) were stirred in using a stirrer for 10 min.

Preparation of Formulation B9:

Phases A and B were each heated separately to 80° C. Phase A was then mixed into phase B with stirring using an homogenizer (2 min at 8000-9000 rpm). The mixture A+B was then stirred under cold conditions. Below 40° C., phase F was mixed in to the mixture A+B using the homogenizer (1 min at 9000 rpm). Phase D (pigments) was then stirred in for 10 min.

Note on the preparation of phase F: copolymer 1 was dissolved in the ethanol and the Euxyl PE 9010 was mixed in.

Example 16

Rapid Water Resistance Test

With the help of an eyeliner applicator, a stroke of each of the formulations V15, V16 and B9 was made on a glass plate as is customarily made on the eyelid. The three strokes of the three samples were applied alongside one another on the same glass plate. The glass plate was placed in a beaker filled with cold drinking water and left in the water thus at room temperature for more than 60 hours. Upon removing the plate, the strokes of formulations V15 and V16 immediately dissolved away. The stroke of formulation B9 still firmly adhered to the plate. Only when it had been rubbed using a finger did the stroke of formulation B9 dissolve.

Example 17

Determination of the Water Resistance According to the in vitro Contact Angle Measurement on Pmma Plates in Accordance with the Measurement Method Described in Example 4.

| Formulation | Contact angle on PMMA plate [°] |
|---|---|
| V15 | 47.1 |
| V16 | 53.4 |
| B9 | 105.9 |

The results of the contact angle measurement method indicate here that formulations V15 and V16 have similar and moderate contact angles. The contact angle for formulation B9 is very large and significantly larger than the contact angles of formulations B15 and B16. Formulation B9 containing copolymer 1 is thus significantly more water-resistant than the placebo (formulation V16) and formulation V15 containing Luviset Shape. This has already been demonstrated in the rapid water resistance test (example 16).

Further Formulation Examples:

The following cosmetic formulations are prepared by the person skilled in the art in a known manner.

In the formulations below, the following meanings apply:

*: particulate organic UV filter in the form of an aqueous dispersion, where the particles have particle sizes of from 50 to 200 nm; the % by weight data in the tables refer only to the active ingredient (UV filter).

**: particulate organic UV filter, where the active ingredient is present in encapsulated form and the particles have particle sizes of from 50 to 200 nm; the % by weight data in the tables refer only to the active ingredient (UV filter).

***: particulate inorganic UV filter, where the particles have particle sizes of from 50 to 200 nm; the % by weight data in the tables refer only to the active ingredient.

Merocyanines of the Formula (A) or (B):

Merocyanine derivatives, as described in WO 2004006878, which correspond to the formula (A) or (B), which may both be present in their E or Z configurations.

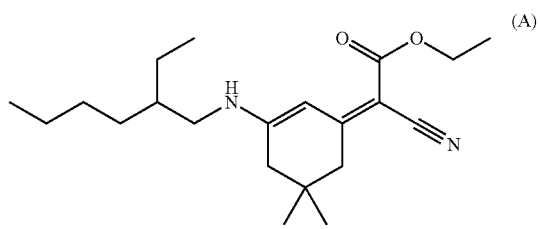

(A)

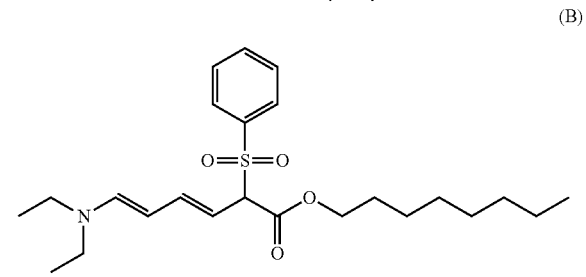

(B)

Malonates of the Formula (C) or (D):

Benzylidene malonate UVB filters which correspond to the formula (C) or (D).

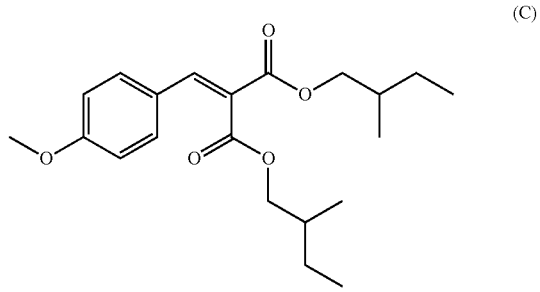

(C)

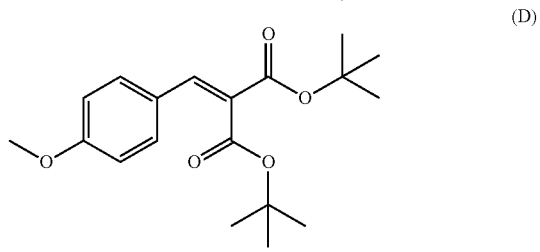

(D)

Water-resistant Sunscreen Emulsions

| | INCI name | A % w/w | B % w/w | C % w/w | D % w/w | E % w/w | F % w/w | G % w/w | H % w/w | I % w/w |
|---|---|---|---|---|---|---|---|---|---|---|
| Part A | Polyglyceryl-10 Pentastearate (and) Behenyl Alcohol (and) Sodium Stearoyl Lactylate | 2.5 | 2.5 | 2.5 | 2.5 | 2.5 | 2.5 | 2.5 | 2.5 | 2.5 |
| | Phenethyl Benzoate | 4.0 | 4.0 | 4.0 | 4.0 | 4.0 | 4.0 | 4.0 | 4.0 | 4.0 |
| | Triisodecyl Trimellitate | 3.0 | 3.0 | 3.0 | 3.0 | 3.0 | 3.0 | 3.0 | 3.0 | 3.0 |
| | Caprylic/Capric/Succinic Triglyceride | 1.0 | 1.0 | 1.0 | 1.0 | 1.0 | 1.0 | 1.0 | 1.0 | 1.0 |
| | Stearyl Alcohol | 1.5 | 1.5 | 1.5 | 1.5 | 1.5 | 1.5 | 1.5 | 1.5 | 1.5 |
| | Squalane | 2.5 | 2.5 | 2.5 | 2.5 | 2.5 | 2.5 | 2.5 | 2.5 | 2.5 |
| | C12-15 Alkyl Benzoate | 2.5 | 2.5 | 2.5 | 2.5 | 2.5 | 2.5 | 2.5 | 2.5 | 2.5 |
| | Diethylamino Hydroxy Benzoyl Hexyl Benzoate | 4.0 | 4.0 | 4.0 | 4.0 | 4.0 | 4.0 | 4.0 | 4.0 | 4.0 |
| | Ethylhexyl Triazone | 2.0 | | 2.0 | | 2.0 | | 2.0 | | 2.0 |
| | Ethylhexyl Methoxycinnamate | 0.0 | 7.0 | | 7.0 | | 7.0 | | 7.0 | 7.0 |
| | Bis-Ethylhexyloxyphenol Methoxyphenyl Triazine | 0.0 | | 2.0 | 2.0 | | | 2.0 | 2.0 | 2.0 |
| Part B | Aqua | qs to 100 | qs to 100 | qs to 100 | qs to 100 | qs to 100 | qs to 100 | qs to 100 | qs to 100 | qs to 100 |
| | Glycerin | 1.8 | 1.8 | 1.8 | 1.8 | 1.8 | 1.8 | 1.8 | 1.8 | 1.8 |
| | Steareth-10 Allyl Ether/Acrylates Copolymer | 0.8 | 0.8 | 0.8 | 0.8 | 0.8 | 0.8 | 0.8 | 0.8 | 0.8 |
| | Methylene Bis-Benzotriazolyl Tetramethylbutyl-phenol * | 0.0 | | | | 3.0 | 3.0 | 3.0 | 3.0 | |
| | Copolymer 1 | 2.0 | 2.0 | 2.0 | 2.0 | 2.0 | 2.0 | 2.0 | 2.0 | 2.0 |
| Part C | Cyclomethicone | 1.5 | 1.5 | 1.5 | 1.5 | 1.5 | 1.5 | 1.5 | 1.5 | 1.5 |
| | Phenoxyethanol (and) Methylparaben (and) Ethylparaben (and) Butylparaben (and) Propylparaben (and) Isobutylparaben | 0.7 | 0.7 | 0.7 | 0.7 | 0.7 | 0.7 | 0.7 | 0.7 | 0.7 |
| | Aqua (and) Tocopheryl Acetate (and) Caprylic/Capric Triglyceride (and) Polysorbate 80 (and) Lecithin | 3.5 | 3.5 | 3.5 | 3.5 | 3.5 | 3.5 | 3.5 | 3.5 | 3.5 |
| | Fragrance | qs | qs | qs | qs | qs | qs | qs | qs | qs |
| | Water (and) Sodium Hydroxide | qs | qs | qs | qs | qs | qs | qs | qs | qs |

Water-resistant Sunscreen Creams

| | INCI name | A % w/w | B % w/w | C % w/w | D % w/w | E % w/w | F % w/w | G % w/w | H % w/w | I % w/w |
|---|---|---|---|---|---|---|---|---|---|---|
| Part A | Tribehenin PEG-20 esters | 5.0 | 5.0 | 5.0 | 5.0 | 5.0 | 5.0 | 5.0 | 5.0 | 5.0 |
| | Phenethyl Benzoate | 4.0 | 4.0 | 4.0 | 4.0 | 4.0 | 4.0 | 4.0 | 4.0 | 4.0 |
| | Tridecyl Trimellitate | 3.0 | 3.0 | 3.0 | 3.0 | 3.0 | 3.0 | 3.0 | 3.0 | 3.0 |
| | Propylheptyl Caprylate | 1.0 | 1.0 | 1.0 | 1.0 | 1.0 | 1.0 | 1.0 | 1.0 | 1.0 |
| | Dibutyl Adipate | 2.0 | 2.0 | 2.0 | 2.0 | 2.0 | 2.0 | 2.0 | 2.0 | 2.0 |

-continued

| | INCI name | A % w/w | B % w/w | C % w/w | D % w/w | E % w/w | F % w/w | G % w/w | H % w/w | I % w/w |
|---|---|---|---|---|---|---|---|---|---|---|
| | PPG-2 Myristyl Ether Propionate | 2.0 | 2.0 | 2.0 | 2.0 | 2.0 | 2.0 | 2.0 | 2.0 | 2.0 |
| | Diethylamino Hydroxy Benzoyl Hexyl Benzoate | 4.0 | 4.0 | 4.0 | 4.0 | 4.0 | 4.0 | 4.0 | 4.0 | 4.0 |
| | Ethylhexyl Triazone | 2.0 | 2.0 | | | | | 2.0 | 2.0 | 2.0 |
| | Ethylhexyl Methoxycinnamate | 7.0 | 7.0 | | | | | | | |
| | Bis-Ethylhexyloxy-phenol Methoxyphenyl Triazine | 0.0 | 2.0 | | 2.0 | | 2.0 | 2.0 | | 2.0 |
| | Malonates of the formula (C) or (D) | 0.0 | 10.0 | 10.0 | 10.0 | 10.0 | 10.0 | 10.0 | 10.0 | 10.0 |
| Part B | Aqua | qs to 100 | qs to 100 | qs to 100 | qs to 100 | qs to 100 | qs to 100 | qs to 100 | qs to 100 | qs to 100 |
| | VP/Dimethylamino ethylmethacrylate/Polycarbamyl Polyglycol Ester | 3.0 | 3.0 | 3.0 | 3.0 | 3.0 | 3.0 | 3.0 | 3.0 | 3.0 |
| | Disodium EDTA | 0.2 | 0.2 | 0.2 | 0.2 | 0.2 | 0.2 | 0.2 | 0.2 | 0.2 |
| | Sclerotium Gum | 2.0 | 2.0 | 2.0 | 2.0 | 2.0 | 2.0 | 2.0 | 2.0 | 2.0 |
| | Ammonium Acryloyldimethyltaurate/Beheneth-25 Methacrylate Crosspolymer | 0.5 | 0.5 | 0.5 | 0.5 | 0.5 | 0.5 | 0.5 | 0.5 | 0.5 |
| | Methylene Bis-Benzotriazolyl Tetramethylbutylphenol * | 3.0 | 3.0 | | | 3.0 | 3.0 | | 3.0 | 3.0 |
| | Copolymer 1 | 2.0 | 2.0 | 2.0 | 2.0 | 2.0 | 2.0 | 2.0 | 2.0 | 2.0 |
| Part C | Cyclopentasiloxane (and) Cyclohexasiloxane | 4.0 | 4.0 | 4.0 | 4.0 | 4.0 | 4.0 | 4.0 | 4.0 | 4.0 |
| | Phenoxyethanol (and) Methylparaben (and) Ethylparaben (and) Butylparaben (and) Propylparaben (and) Isobutylparaben | 1.0 | 1.0 | 1.0 | 1.0 | 1.0 | 1.0 | 1.0 | 1.0 | 1.0 |
| | Sodium Hydroxide (and) Water | qsp | qsp | qsp | qsp | qsp | qsp | qsp | qsp | qsp |

Water-resistant Gel Creams

| INCI name | A % w/w | B % w/w | C % w/w | D % w/w | E % w/w | F % w/w | G % w/w | H % w/w | I % w/w |
|---|---|---|---|---|---|---|---|---|---|
| Sodium Carbomer | 0.5 | 0.5 | 0.5 | 0.5 | 0.5 | 0.5 | 0.5 | 0.5 | 0.5 |
| Xanthan Gum | 0.2 | 0.2 | 0.2 | 0.2 | 0.2 | 0.2 | 0.2 | 0.2 | 0.2 |
| Phenethyl Benzoate | 4.0 | 4.0 | 4.0 | 4.0 | 4.0 | 4.0 | 4.0 | 4.0 | 4.0 |
| Triisodecyl Trimellitate | 3.0 | 3.0 | 3.0 | 3.0 | 3.0 | 3.0 | 3.0 | 3.0 | 3.0 |
| Propylene Glycol Dibenzoate | 1.0 | 1.0 | 1.0 | 1.0 | 1.0 | 1.0 | 1.0 | 1.0 | 1.0 |
| Glycerin | 5.0 | 5.0 | 5.0 | 5.0 | 5.0 | 5.0 | 5.0 | 5.0 | 5.0 |
| Tocopherol | 0.3 | 0.3 | 0.3 | 0.3 | 0.3 | 0.3 | 0.3 | 0.3 | 0.3 |
| Trisodium EDTA | 0.5 | 0.5 | 0.5 | 0.5 | 0.5 | 0.5 | 0.5 | 0.5 | 0.5 |
| Alcohol | 7.5 | 7.5 | 7.5 | 7.5 | 7.5 | 7.5 | 7.5 | 7.5 | 7.5 |
| Aqua | ad 100 | ad 100 | ad 100 | ad 100 | ad 100 | ad 100 | ad 100 | ad 100 | ad 100 |
| Diethylamino Hydroxy Benzoyl Hexyl Benzoate | 4.0 | 4.0 | 4.0 | 4.0 | 4.0 | 4.0 | 4.0 | 4.0 | 4.0 |
| Ethylhexyl Triazone | 2.0 | | 2.0 | | 2.0 | | 2.0 | | 2.0 |
| Ethylhexyl Methoxycinnamate | 0.0 | 7.0 | | 7.0 | | 7.0 | | 7.0 | 7.0 |

-continued

| INCI name | A % w/w | B % w/w | C % w/w | D % w/w | E % w/w | F % w/w | G % w/w | H % w/w | I % w/w |
|---|---|---|---|---|---|---|---|---|---|
| Bis-Ethylhexyloxyphenol Methoxyphenyl Triazine | 0.0 | | 2.0 | 2.0 | | | 2.0 | 2.0 | 2.0 |
| Methylene Bis-Benzotriazolyl Tetramethylbutylphenol * | 0.0 | | | | 3.0 | 3.0 | 3.0 | 3.0 | |
| Bis-Ethylhexyloxyphenol Methoxyphenyl Triazine ** | 2.0 | 2.0 | 2.0 | 2.0 | 2.0 | 2.0 | 2.0 | 2.0 | 2.0 |
| Copolymer 1 | 2.0 | 2.0 | 2.0 | 2.0 | 2.0 | 2.0 | 2.0 | 2.0 | 2.0 |

Water-resistant Emulsifier-free Sunscreen Formulations

| INCI name | A % w/w | B % w/w | C % w/w | D % w/w | E % w/w | F % w/w | G % w/w | H % w/w | I % w/w |
|---|---|---|---|---|---|---|---|---|---|
| Acrylates/C10-30 Alkyl Acrylate Crosspolymer | 0.1 | 0.1 | 0.1 | 0.1 | 0.1 | 0.1 | 0.1 | 0.1 | 0.1 |
| Xanthan Gum | 0.5 | 0.5 | 0.5 | 0.5 | 0.5 | 0.5 | 0.5 | 0.5 | 0.5 |
| Phenethyl Benzoate | 4.0 | 4.0 | 4.0 | 4.0 | 4.0 | 4.0 | 4.0 | 4.0 | 4.0 |
| Triisodecyl Trimellitate | 2.0 | 2.0 | 2.0 | 2.0 | 2.0 | 2.0 | 2.0 | 2.0 | 2.0 |
| Tridecyl Trimellitate | 2.0 | 2.0 | 2.0 | 2.0 | 2.0 | 2.0 | 2.0 | 2.0 | 2.0 |
| Diethylhexyl Succinate | 1.0 | 1.0 | 1.0 | 1.0 | 1.0 | 1.0 | 1.0 | 1.0 | 1.0 |
| Dimethicone | 3.0 | 3.0 | 3.0 | 3.0 | 3.0 | 3.0 | 3.0 | 3.0 | 3.0 |
| Cyclomethicone | 1.0 | 1.0 | 1.0 | 1.0 | 1.0 | 1.0 | 1.0 | 1.0 | 1.0 |
| Ethylhexylglycerin | 0.5 | 0.5 | 0.5 | 0.5 | 0.5 | 0.5 | 0.5 | 0.5 | 0.5 |
| Glycerin | 2.5 | 2.5 | 2.5 | 2.5 | 2.5 | 2.5 | 2.5 | 2.5 | 2.5 |
| Vitamin E Acetate | 1.0 | 1.0 | 1.0 | 1.0 | 1.0 | 1.0 | 1.0 | 1.0 | 1.0 |
| Polyethylene Terephthalate | 0.2 | 0.2 | 0.2 | 0.2 | 0.2 | 0.2 | 0.2 | 0.2 | 0.2 |
| DMDM Hydantoin | 0.1 | 0.1 | 0.1 | 0.1 | 0.1 | 0.1 | 0.1 | 0.1 | 0.1 |
| Butylene Glycol (and) Iodopropynyl Butylcarbamate | 0.2 | 0.2 | 0.2 | 0.2 | 0.2 | 0.2 | 0.2 | 0.2 | 0.2 |
| Phenoxyethanol | 0.6 | 0.6 | 0.6 | 0.6 | 0.6 | 0.6 | 0.6 | 0.6 | 0.6 |
| Alcohol | 1.0 | 1.0 | 1.0 | 1.0 | 1.0 | 1.0 | 1.0 | 1.0 | 1.0 |
| Fragrance | 0.2 | 0.2 | 0.2 | 0.2 | 0.2 | 0.2 | 0.2 | 0.2 | 0.2 |
| Aqua | ad 100 | ad 100 | ad 100 | ad 100 | ad 100 | ad 100 | ad 100 | ad 100 | ad 100 |
| Diethylamino Hydroxy Benzoyl Hexyl Benzoate | 4.0 | 4.0 | 4.0 | 4.0 | 4.0 | 4.0 | 4.0 | 4.0 | 4.0 |
| Ethylhexyl Triazone | 2.0 | 2.0 | | | | | 2.0 | 2.0 | 2.0 |
| Ethylhexyl Methoxycinnamate | 7.0 | 7.0 | | | | | | | |
| Bis-Ethylhexyloxyphenol Methoxyphenyl Triazine | 0.0 | 2.0 | | 2.0 | | 2.0 | 2.0 | | 2.0 |
| Methylene Bis-Benzotriazolyl Tetramethylbutylphenol * | 3.0 | 3.0 | | | 3.0 | 3.0 | | 3.0 | 3.0 |
| Malonates of the formula (C) or (D) | 0.0 | | 10.0 | 10.0 | 10.0 | 10.0 | 10.0 | 10.0 | 10.0 |
| Bis-Ethylhexyloxyphenol Methoxyphenyl Triazine ** | 2.0 | 2.0 | 2.0 | 2.0 | 2.0 | 2.0 | 2.0 | 2.0 | 2.0 |
| Copolymer 1 | 2.0 | 2.0 | 2.0 | 2.0 | 2.0 | 2.0 | 2.0 | 2.0 | 2.0 |

Water-soluble Sunscreen Sprays

| | INCI name | A % w/w | B % w/w | C % w/w | D % w/w | E % w/w | F % w/w | G % w/w | H % w/w | I % w/w |
|---|---|---|---|---|---|---|---|---|---|---|
| Part A | Cyclopentasiloxane | 2.5 | 2.5 | 2.5 | 2.5 | 2.5 | 2.5 | 2.5 | 2.5 | 2.5 |
| | Hydrogenated Coco-Glycerides | 1.5 | 1.5 | 1.5 | 1.5 | 1.5 | 1.5 | 1.5 | 1.5 | 1.5 |
| | Phenethyl Benzoate | 4.0 | 4.0 | 4.0 | 4.0 | 4.0 | 4.0 | 4.0 | 4.0 | 4.0 |
| | Triisodecyl Trimellitate | 2.0 | 2.0 | 2.0 | 2.0 | 2.0 | 2.0 | 2.0 | 2.0 | 2.0 |
| | Triheptanoin | 1.0 | 1.0 | 1.0 | 1.0 | 1.0 | 1.0 | 1.0 | 1.0 | 1.0 |
| | C12-15 Alkyl Benzoate | 3.6 | 3.6 | 3.6 | 3.6 | 3.6 | 3.6 | 3.6 | 3.6 | 3.6 |
| | Diethylamino Hydroxy Benzoyl Hexyl Benzoate | 4.0 | 4.0 | 4.0 | 4.0 | 4.0 | 4.0 | 4.0 | 4.0 | 4.0 |
| | Ethylhexyl Triazone | 2.0 | | 2.0 | | 2.0 | | 2.0 | | 2.0 |
| | Ethylhexyl Methoxycinnamate | 0.0 | 7.0 | | 7.0 | | 7.0 | | 7.0 | 7.0 |
| | Bis-Ethylhexyloxy-phenol Methoxyphenyl Triazine | 0.0 | | 2.0 | 2.0 | | | 2.0 | 2.0 | 2.0 |
| Part B | Water (and) Caprylic/Capric Triglyceride (and) Glycerin (and) Ceteareth-25 (and) Disodium Ethylene Dicocamide PEG-15 Disulfate (and) Sodium Lauroyl Lactylate (and) Behenyl Alcohol (and) Glyceryl Stearate (and) Glyceryl Stearate Citrate (and) Xanthan Gum | 10.0 | 10.0 | 10.0 | 10.0 | 10.0 | 10.0 | 10.0 | 10.0 | 10.0 |
| | Glycerin | 3.0 | 3.0 | 3.0 | 3.0 | 3.0 | 3.0 | 3.0 | 3.0 | 3.0 |
| | Aqua | qs to 100 | qs to 100 | qs to 100 | qs to 100 | qs to 100 | qs to 100 | qs to 100 | qs to 100 | qs to 100 |
| | Methylene Bis-Benzotriazolyl Tetramethylbutyl-phenol * | 0.0 | | | | 3.0 | 3.0 | 3.0 | 3.0 | |
| | Tris-Biphenyl Triazine * | 2.0 | 2.0 | 2.0 | 2.0 | 2.0 | 2.0 | 2.0 | 2.0 | 2.0 |
| | Copolymer 1 | 2.0 | 2.0 | 2.0 | 2.0 | 2.0 | 2.0 | 2.0 | 2.0 | 2.0 |
| Part C | Alcohol Denat. | 7.0 | 7.0 | 7.0 | 7.0 | 7.0 | 7.0 | 7.0 | 7.0 | 7.0 |
| Part D | Phenoxyethanol (and) Methylparaben (and) Ethylparaben (and) Butylparaben (and) Propylparaben (and) Isobutylparaben | 0.7 | 0.7 | 0.7 | 0.7 | 0.7 | 0.7 | 0.7 | 0.7 | 0.7 |
| | Tocopheryl Acetate | 0.6 | 0.6 | 0.6 | 0.6 | 0.6 | 0.6 | 0.6 | 0.6 | 0.6 |

Water-resistant and Foaming Oil-in-water Sunscreen Lotions

| INCI name | A % w/w | B % w/w | C % w/w | D % w/w | E % w/w | F % w/w | G % w/w | H % w/w | I % w/w |
|---|---|---|---|---|---|---|---|---|---|
| Stearic Acid | 4.0 | 4.0 | 4.0 | 4.0 | 4.0 | 4.0 | 4.0 | 4.0 | 4.0 |
| Myristyl Alcohol | 1.50 | 1.50 | 1.50 | 1.50 | 1.50 | 1.50 | 1.50 | 1.50 | 1.50 |
| Cetearyl Alcohol | 0.5 | 0.5 | 0.5 | 0.5 | 0.5 | 0.5 | 0.5 | 0.5 | 0.5 |
| PEG-100 Stearate | 4.0 | 4.0 | 4.0 | 4.0 | 4.0 | 4.0 | 4.0 | 4.0 | 4.0 |
| Kaolin | 0.05 | 0.05 | 0.05 | 0.05 | 0.05 | 0.05 | 0.05 | 0.05 | 0.05 |
| Hydroxyethylcellulose | 0.05 | 0.05 | 0.05 | 0.05 | 0.05 | 0.05 | 0.05 | 0.05 | 0.05 |
| Magnesium Aluminium Silicate | 0.20 | 0.20 | 0.20 | 0.20 | 0.20 | 0.20 | 0.20 | 0.20 | 0.20 |

| INCI name | A % w/w | B % w/w | C % w/w | D % w/w | E % w/w | F % w/w | G % w/w | H % w/w | I % w/w |
|---|---|---|---|---|---|---|---|---|---|
| Mineral Oil | 8.0 | 8.0 | 8.0 | 8.0 | 8.0 | 8.0 | 8.0 | 8.0 | 8.0 |
| Cyclomethicone | 6.0 | 6.0 | 6.0 | 6.0 | 6.0 | 6.0 | 6.0 | 6.0 | 6.0 |
| Dimethicone | 3.0 | 3.0 | 3.0 | 3.0 | 3.0 | 3.0 | 3.0 | 3.0 | 3.0 |
| PEG-180/Laureth-50/TMMG Copolymer | 0.5 | 0.5 | 0.5 | 0.5 | 0.5 | 0.5 | 0.5 | 0.5 | 0.5 |
| Glycerin | 3.0 | 3.0 | 3.0 | 3.0 | 3.0 | 3.0 | 3.0 | 3.0 | 3.0 |
| Hydrogenated Coco-Glycerides | 5.0 | 5.0 | 5.0 | 5.0 | 5.0 | 5.0 | 5.0 | 5.0 | 5.0 |
| Fragrance | q.s. | q.s. | q.s. | q.s. | q.s. | q.s. | q.s. | q.s. | q.s. |
| Aqua | ad 100 | ad 100 | ad 100 | ad 100 | ad 100 | ad 100 | ad 100 | ad 100 | ad 100 |
| pH adjusted to 5.0-6.5 | | | | | | | | | |
| Propellant | qs | qs | qs | qs | qs | qs | qs | qs | qs |
| Diethylamino Hydroxy Benzoyl Hexyl Benzoate | 4.0 | 4.0 | 4.0 | 4.0 | 4.0 | 4.0 | 4.0 | 4.0 | 4.0 |
| Ethylhexyl Triazone | 2.0 | 2.0 | | | | | 2.0 | 2.0 | 2.0 |
| Ethylhexyl Methoxycinnamate | 7.0 | 7.0 | | | | | | | |
| Bis-Ethylhexyloxyphenol Methoxyphenyl Triazine | 0.0 | 2.0 | | 2.0 | | 2.0 | 2.0 | | 2.0 |
| Methylene Bis-Benzotriazolyl Tetramethylbutylphenol * | 3.0 | 3.0 | | 3.0 | 3.0 | | 3.0 | 3.0 | |
| Malonates of the formula (C) or (D) | 0.0 | | 10.0 | 10.0 | 10.0 | 10.0 | 10.0 | 10.0 | 10.0 |
| Tris-Biphenyl Triazine * | 2.0 | 2.0 | 2.0 | 2.0 | 2.0 | 2.0 | 2.0 | 2.0 | 2.0 |
| Copolymer 1 | 2.0 | 2.0 | 2.0 | 2.0 | 2.0 | 2.0 | 2.0 | 2.0 | 2.0 |

Water-resistant Lipsticks

| INCI name | A % w/w | B % w/w | C % w/w | D % w/w | E % w/w | F % w/w | G % w/w | H % w/w | I % w/w |
|---|---|---|---|---|---|---|---|---|---|
| Microcrystalline Wax | 7.0 | 7.0 | 7.0 | 7.0 | 7.0 | 7.0 | 7.0 | 7.0 | 7.0 |
| *Copernicia Cerifera* (Carnauba) Wax | 2.5 | 2.5 | 2.5 | 2.5 | 2.5 | 2.5 | 2.5 | 2.5 | 2.5 |
| Candelilla Cera | 6.5 | 6.5 | 6.5 | 6.5 | 6.5 | 6.5 | 6.5 | 6.5 | 6.5 |
| Cetyl Alcohol | 1.5 | 1.5 | 1.5 | 1.5 | 1.5 | 1.5 | 1.5 | 1.5 | 1.5 |
| Lanolin Oil | 9.0 | 9.0 | 9.0 | 9.0 | 9.0 | 9.0 | 9.0 | 9.0 | 9.0 |
| Bis-Diglyceryl Polyacyladipate-2 | 4.0 | 4.0 | 4.0 | 4.0 | 4.0 | 4.0 | 4.0 | 4.0 | 4.0 |
| *Persea Gratissima* (Avocado) Oil | 5.0 | 5.0 | 5.0 | 5.0 | 5.0 | 5.0 | 5.0 | 5.0 | 5.0 |
| Pentaerythrityl Tetraisostearate | 2.0 | 2.0 | 2.0 | 2.0 | 2.0 | 2.0 | 2.0 | 2.0 | 2.0 |
| Myristyl Lactate | 6.0 | 6.0 | 6.0 | 6.0 | 6.0 | 6.0 | 6.0 | 6.0 | 6.0 |
| *Simmondsia Chinensis* (Jojoba) Seed Oil | 2.0 | 2.0 | 2.0 | 2.0 | 2.0 | 2.0 | 2.0 | 2.0 | 2.0 |
| Hydrogenated Polydecene | 13.0 | 13.0 | 13.0 | 13.0 | 13.0 | 13.0 | 13.0 | 13.0 | 13.0 |
| PEG-45/Dodecyl Glycol Copolymer | 1.0 | 1.0 | 1.0 | 1.0 | 1.0 | 1.0 | 1.0 | 1.0 | 1.0 |
| Interference Pigments | 6.8 | 6.8 | 6.8 | 6.8 | 6.8 | 6.8 | 6.8 | 6.8 | 6.8 |
| Tocopheryl Acetate | 1.0 | 1.0 | 1.0 | 1.0 | 1.0 | 1.0 | 1.0 | 1.0 | 1.0 |
| BHT | 0.03 | 0.03 | 0.03 | 0.03 | 0.03 | 0.03 | 0.03 | 0.03 | 0.03 |
| Preservatives | q.s. | q.s. | q.s. | q.s. | q.s. | q.s. | q.s. | q.s. | q.s. |
| Fragrance. Aroma | q.s. | q.s. | q.s. | q.s. | q.s. | q.s. | q.s. | q.s. | q.s. |
| Aqua | qs to 100 | qs to 100 | qs to 100 | qs to 100 | qs to 100 | qs to 100 | qs to 100 | qs to 100 | qs to 100 |
| Diethylamino Hydroxy Benzoyl Hexyl Benzoate | 4.0 | 4.0 | 4.0 | 4.0 | 4.0 | 4.0 | 4.0 | 4.0 | 4.0 |

-continued

| INCI name | A % w/w | B % w/w | C % w/w | D % w/w | E % w/w | F % w/w | G % w/w | H % w/w | I % w/w |
|---|---|---|---|---|---|---|---|---|---|
| Ethylhexyl Triazone | 2.0 | | 2.0 | | 2.0 | | 2.0 | | 2.0 |
| Ethylhexyl Methoxycinnamate | 0.0 | 7.0 | | 7.0 | | 7.0 | | 7.0 | 7.0 |
| Bis-Ethylhexyloxyphenol Methoxyphenyl Triazine | 0.0 | | 2.0 | 2.0 | | | 2.0 | 2.0 | 2.0 |
| Methylene Bis-Benzotriazolyl Tetramethylbutyl-phenol * | 0.0 | | | | 3.0 | 3.0 | 3.0 | 3.0 | |
| Methanone, 1,1'-(1,4-piperazinediyl)bis[1-[2-[4-(diethylamino)-2-hydroxybenzoyl]phenyl] CAS number (919803-06-8) * | 2.0 | 2.0 | 2.0 | 2.0 | 2.0 | 2.0 | 2.0 | 2.0 | 2.0 |
| Copolymer 1 | 2.0 | 2.0 | 2.0 | 2.0 | 2.0 | 2.0 | 2.0 | 2.0 | 2.0 |

25

Water-resistant Water-in-oil Emulsions

| | INCI name | A % w/w | B % w/w | C % w/w | D % w/w | E % w/w | F % w/w | G % w/w | H % w/w | I % w/w |
|---|---|---|---|---|---|---|---|---|---|---|
| Part A | Polyglyceryl-10 Pentastearate (and) Behenyl Alcohol (and) Sodium Stearoyl Lactylate | 2.5 | 2.5 | 2.5 | 2.5 | 2.5 | 2.5 | 2.5 | 2.5 | 2.5 |
| | Stearyl Alcohol | 1.5 | 1.5 | 1.5 | 1.5 | 1.5 | 1.5 | 1.5 | 1.5 | 1.5 |
| | Squalane | 4.0 | 4.0 | 4.0 | 4.0 | 4.0 | 4.0 | 4.0 | 4.0 | 4.0 |
| | C12-15 Alkyl Benzoate | 5.5 | 5.5 | 5.5 | 5.5 | 5.5 | 5.5 | 5.5 | 5.5 | 5.5 |
| | Diethylamino Hydroxy Benzoyl Hexyl Benzoate | 4.0 | 4.0 | 4.0 | 4.0 | 4.0 | 4.0 | 4.0 | 4.0 | 4.0 |
| | Ethylhexyl Triazone | 2.0 | 2.0 | | | | | 2.0 | 2.0 | 2.0 |
| | Ethylhexyl Methoxycinnamate | 7.0 | 7.0 | | | | | | | |
| | Bis-Ethylhexyloxyphenol Methoxyphenyl Triazine | 0.0 | 2.0 | | 2.0 | | 2.0 | 2.0 | | 2.0 |
| | Malonates of the formula (C) or (D) | 0.0 | 10.0 | 10.0 | 10.0 | 10.0 | 10.0 | 10.0 | 10.0 | 10.0 |
| Part B | Aqua | qs to 100 | qs to 100 | qs to 100 | qs to 100 | qs to 100 | qs to 100 | qs to 100 | qs to 100 | qs to 100 |
| | Methylene Bis-Benzotriazolyl Tetramethylbutyl-phenol * | 3.0 | 3.0 | | | 3.0 | 3.0 | | 3.0 | 3.0 |
| | Methanone, 1,1'-(1,4-piperazinediyl)bis[1-[2-[4-(diethylamino)-2-hydroxybenzoyl]phenyl] CAS number (919803-06-8) * | 2.0 | 2.0 | 2.0 | 2.0 | 2.0 | 2.0 | 2.0 | 2.0 | 2.0 |
| | Copolymer 1 | 2.0 | 2.0 | 2.0 | 2.0 | 2.0 | 2.0 | 2.0 | 2.0 | 2.0 |
| Part C | Glycerin | 1.8 | 1.8 | 1.8 | 1.8 | 1.8 | 1.8 | 1.8 | 1.8 | 1.8 |
| | Steareth-10 Allyl Ether/Acrylates Copolymer | 0.8 | 0.8 | 0.8 | 0.8 | 0.8 | 0.8 | 0.8 | 0.8 | 0.8 |

|  | INCI name | A % w/w | B % w/w | C % w/w | D % w/w | E % w/w | F % w/w | G % w/w | H % w/w | I % w/w |
|---|---|---|---|---|---|---|---|---|---|---|
|  | Citric Acid (and) Silver Citrate | 0.1 | 0.1 | 0.1 | 0.1 | 0.1 | 0.1 | 0.1 | 0.1 | 0.1 |
|  | Sclerotium Gum | 0.1 | 0.1 | 0.1 | 0.1 | 0.1 | 0.1 | 0.1 | 0.1 | 0.1 |
| Part D | Cyclomethicone | 1.5 | 1.5 | 1.5 | 1.5 | 1.5 | 1.5 | 1.5 | 1.5 | 1.5 |
| Part E | Aqua (and) Tocopheryl Acetate (and) Caprylic/Capric Triglyceride (and) Polysorbate 80 (and) Lecithin | 3.5 | 3.5 | 3.5 | 3.5 | 3.5 | 3.5 | 3.5 | 3.5 | 3.5 |
|  | Fragrance | qs | qs | qs | qs | qs | qs | qs | qs | qs |
|  | Water (and) Sodium Hydroxide | qs | qs | qs | qs | qs | qs | qs | qs | qs |

Water-resistant Water/Silicone Sunscreen Lotions

|  | INCI name | A % w/w | B % w/w | C % w/w | D % w/w | E % w/w | F % w/w | G % w/w | H % w/w | I % w/w |
|---|---|---|---|---|---|---|---|---|---|---|
| Part A | Polyglyceryl-4 Isostearate and Cetyl PEG/PPG-10/1 Dimethicone and Hexyl Laurate | 10.0 | 10.0 | 10.0 | 10.0 | 10.0 | 10.0 | 10.0 | 10.0 | 10.0 |
|  | Polyglyceryl-3 Distearate | 0.6 | 0.6 | 0.6 | 0.6 | 0.6 | 0.6 | 0.6 | 0.6 | 0.6 |
|  | Tribehenin | 3.0 | 3.0 | 3.0 | 3.0 | 3.0 | 3.0 | 3.0 | 3.0 | 3.0 |
|  | Cetyl Dimethicone | 2.0 | 2.0 | 2.0 | 2.0 | 2.0 | 2.0 | 2.0 | 2.0 | 2.0 |
|  | C12-15 Alkyl Benzoate | 5.0 | 5.0 | 5.0 | 5.0 | 5.0 | 5.0 | 5.0 | 5.0 | 5.0 |
|  | Cyclomethicone | 8.9 | 8.9 | 8.9 | 8.9 | 8.9 | 8.9 | 8.9 | 8.9 | 8.9 |
|  | Phenyl trimethicone | 7.9 | 7.9 | 7.9 | 7.9 | 7.9 | 7.9 | 7.9 | 7.9 | 7.9 |
|  | Diethylamino Hydroxy Benzoyl Hexyl Benzoate | 4.0 | 4.0 | 4.0 | 4.0 | 4.0 | 4.0 | 4.0 | 4.0 | 4.0 |
|  | Ethylhexyl Triazone | 2.0 | 2.0 |  |  |  |  | 2.0 | 2.0 | 2.0 |
|  | Ethylhexyl Methoxycinnamate | 7.0 | 7.0 |  |  |  |  |  |  |  |
|  | Bis-Ethylhexyloxy-phenol Methoxyphenyl Triazine | 0.0 | 2.0 |  | 2.0 |  | 2.0 | 2.0 |  | 2.0 |
|  | Malonates of the formula (C) or (D) | 0.0 |  | 10.0 | 10.0 | 10.0 | 10.0 | 10.0 | 10.0 | 10.0 |
| Part B | Xanthan Gum | 0.1 | 0.1 | 0.1 | 0.1 | 0.1 | 0.1 | 0.1 | 0.1 | 0.1 |
|  | Glycerin | 3.0 | 3.0 | 3.0 | 3.0 | 3.0 | 3.0 | 3.0 | 3.0 | 3.0 |
|  | Aqua | qsp 100 | qsp 100 | qsp 100 | qsp 100 | qsp 100 | qsp 100 | qsp 100 | qsp 100 | qsp 100 |
|  | Disodium EDTA | 0.1 | 0.1 | 0.1 | 0.1 | 0.1 | 0.1 | 0.1 | 0.1 | 0.1 |
|  | Methylene Bis-Benzotriazolyl Tetramethylbutyl-phenol * | 3.0 | 3.0 |  | 3.0 | 3.0 |  | 3.0 | 3.0 |  |
|  | Bis-Ethylhexyloxy-phenol Methoxyphenyl Triazine ** | 2.0 | 2.0 | 2.0 | 2.0 | 2.0 | 2.0 | 2.0 | 2.0 | 2.0 |
|  | Tris-Biphenyl Triazine * | 2.0 | 2.0 | 2.0 | 2.0 | 2.0 | 2.0 | 2.0 | 2.0 | 2.0 |
|  | Methanone, 1,1'-(1,4-piperazinediyl)bis[1-[2-[4-(diethylamino)-2-hydroxybenzoyl]phenyl]-CAS | 2.0 | 2.0 | 2.0 | 2.0 | 2.0 | 2.0 | 2.0 | 2.0 | 2.0 |

-continued

| | INCI name | A % w/w | B % w/w | C % w/w | D % w/w | E % w/w | F % w/w | G % w/w | H % w/w | I % w/w |
|---|---|---|---|---|---|---|---|---|---|---|
| | number (919803-06-8) * | | | | | | | | | |
| | Copolymer 1 | 2.0 | 2.0 | 2.0 | 2.0 | 2.0 | 2.0 | 2.0 | 2.0 | 2.0 |
| Part C | Citric Acid (and) Silver Citrate | 0.0 | 0.1 | 0.2 | 0.3 | 0.5 | 0.6 | 0.8 | 0.9 | 1.0 |
| | Sodium Chloride | 1.0 | 1.0 | 1.0 | 1.0 | 1.0 | 1.0 | 1.0 | 1.0 | 1.0 |
| | Tocopheryl Acetate | 0.5 | 0.5 | 0.5 | 0.5 | 0.5 | 0.5 | 0.5 | 0.5 | 0.5 |
| | Fragrance | q.s. | q.s. | q.s. | q.s. | q.s. | q.s. | q.s. | q.s. | q.s. |

Water-resistant Gels

| INCI name | A % w/w | B % w/w | C % w/w | D % w/w | E % w/w | F % w/w | G % w/w | H % w/w | I % w/w |
|---|---|---|---|---|---|---|---|---|---|
| Phenethyl Benzoate | 2.0 | 2.0 | 2.0 | 2.0 | 2.0 | 2.0 | 2.0 | 2.0 | 2.0 |
| Triisodecyl Trimellitate | 1.0 | 1.0 | 1.0 | 1.0 | 1.0 | 1.0 | 1.0 | 1.0 | 1.0 |
| PPG-3 Myristyl Ether | 0.5 | 0.5 | 0.5 | 0.5 | 0.5 | 0.5 | 0.5 | 0.5 | 0.5 |
| Anhydrous Ethanol | qsp 100 | qsp 100 | qsp 100 | qsp 100 | qsp 100 | qsp 100 | qsp 100 | qsp 100 | qsp 100 |
| Hydroxypropyl Methylcellulose | 1.0 | 1.0 | 1.0 | 1.0 | 1.0 | 1.0 | 1.0 | 1.0 | 1.0 |
| Acrylates/Octyl-acrylamide Copolymer | 1.0 | 1.0 | 1.0 | 1.0 | 1.0 | 1.0 | 1.0 | 1.0 | 1.0 |
| C12-15 Alkyl Benzoate | 10.0 | 10.0 | 10.0 | 10.0 | 10.0 | 10.0 | 10.0 | 10.0 | 10.0 |
| Cyclomethicone | 3.0 | 3.0 | 3.0 | 3.0 | 3.0 | 3.0 | 3.0 | 3.0 | 3.0 |
| PEG/PPG-4/12 Dimethicone | 1.0 | 1.0 | 1.0 | 1.0 | 1.0 | 1.0 | 1.0 | 1.0 | 1.0 |
| Citric Acid (and) Silver Citrate | 0.1 | 0.1 | 0.1 | 0.1 | 0.1 | 0.1 | 0.1 | 0.1 | 0.1 |
| Sclerotium Gum | 0.1 | 0.1 | 0.1 | 0.1 | 0.1 | 0.1 | 0.1 | 0.1 | 0.1 |
| Diethylamino Hydroxy Benzoyl Hexyl Benzoate | 4.0 | 4.0 | 4.0 | 4.0 | 4.0 | 4.0 | 4.0 | 4.0 | 4.0 |
| Ethylhexyl Triazone | 2.0 | | 2.0 | | 2.0 | | 2.0 | | 2.0 |
| Ethylhexyl Methoxycinnamate | 0.0 | 7.0 | | 7.0 | | 7.0 | | 7.0 | 7.0 |
| Bis-Ethylhexyloxy-phenol Methoxyphenyl Triazine | 0.0 | 2.0 | 2.0 | | | 2.0 | 2.0 | 2.0 | |
| Methylene Bis-Benzotriazolyl Tetramethylbutyl-phenol * | 0.0 | | | 3.0 | 3.0 | 3.0 | 3.0 | | |
| Titanium Dioxide *** | 2.0 | 2.0 | 2.0 | 2.0 | 2.0 | 2.0 | 2.0 | 2.0 | 2.0 |
| Copolymer 1 | 2.0 | 2.0 | 2.0 | 2.0 | 2.0 | 2.0 | 2.0 | 2.0 | 2.0 |

Water-resistant Clear Gels

| INCI name | A % w/w | B % w/w | C % w/w | D % w/w | E % w/w | F % w/w | G % w/w | H % w/w | I % w/w |
|---|---|---|---|---|---|---|---|---|---|
| SD Alcohol 40 | 68.0 | 68.0 | 68.0 | 68.0 | 68.0 | 68.0 | 68.0 | 68.0 | 68.0 |
| Hydroxypropyl Cellulose | 1.7 | 1.7 | 1.7 | 1.7 | 1.7 | 1.7 | 1.7 | 1.7 | 1.7 |
| Isopropyl PPG-2 Isodeceth-7 Carboxylate | 9.6 | 9.6 | 9.6 | 9.6 | 9.6 | 9.6 | 9.6 | 9.6 | 9.6 |
| Fragrance | 0.6 | 0.6 | 0.6 | 0.6 | 0.6 | 0.6 | 0.6 | 0.6 | 0.6 |
| Aqua | qsp 100 | qsp 100 | qsp 100 | qsp 100 | qsp 100 | qsp 100 | qsp 100 | qsp 100 | qsp 100 |

-continued

| INCI name | A % w/w | B % w/w | C % w/w | D % w/w | E % w/w | F % w/w | G % w/w | H % w/w | I % w/w |
|---|---|---|---|---|---|---|---|---|---|
| Citric Acid (and) Silver Citrate | 0.1 | 0.1 | 0.1 | 0.1 | 0.1 | 0.1 | 0.1 | 0.1 | 0.1 |
| Sclerotium Gum | 0.1 | 0.1 | 0.1 | 0.1 | 0.1 | 0.1 | 0.1 | 0.1 | 0.1 |
| Merocyanines of the formula (A) or (B) | 1.0 | 1.0 | 1.0 | 1.0 | 1.0 | 1.0 | 1.0 | 1.0 | 1.0 |
| Diethylamino Hydroxy Benzoyl Hexyl Benzoate | 4.0 | 4.0 | 4.0 | 4.0 | 4.0 | 4.0 | 4.0 | 4.0 | 4.0 |
| Ethylhexyl Triazone | 2.0 | | 2.0 | | 2.0 | | 2.0 | | 2.0 |
| Ethylhexyl Methoxycinnamate | 0.0 | 7.0 | | 7.0 | | 7.0 | | 7.0 | 7.0 |
| Bis-Ethylhexyloxy-phenol Methoxyphenyl Triazine | 0.0 | | 2.0 | 2.0 | | | 2.0 | 2.0 | 2.0 |
| Copolymer 1 | 2.0 | 2.0 | 2.0 | 2.0 | 2.0 | 2.0 | 2.0 | 2.0 | 2.0 |

Water-resistant Silicone/Water Sunscreen Creams

| | INCI name | A % w/w | B % w/w | C % w/w | D % w/w | E % w/w | F % w/w | G % w/w | H % w/w | I % w/w |
|---|---|---|---|---|---|---|---|---|---|---|
| Part A | Cyclopentasiloxane (and) Dimethicone/Vinyl Dimethicone Crosspolymer | 8.0 | 8.0 | 8.0 | 8.0 | 8.0 | 8.0 | 8.0 | 8.0 | 8.0 |
| | Dimethicone (and) Dimethicone/Vinyl Dimethicone Crosspolymer | 30.0 | 30.0 | 30.0 | 30.0 | 30.0 | 30.0 | 30.0 | 30.0 | 30.0 |
| | Cyclopentasiloxane | 10.0 | 10.0 | 10.0 | 10.0 | 10.0 | 10.0 | 10.0 | 10.0 | 10.0 |
| | Butyl Methoxydibenzoyl methane | 3.0 | 3.0 | 3.0 | 3.0 | 3.0 | 3.0 | 3.0 | 3.0 | 3.0 |
| | Octocrylene | 0.0 | 8.0 | | 8.0 | | 8.0 | | 8.0 | 8.0 |
| | Ethylhexyl Salicylate | 0.0 | | 5.0 | 5.0 | | | | | 5.0 |
| | Diethylhexyl Butamido Triazone | 0.0 | | | | 1.0 | 1.0 | | | 1.0 |
| | Ethylhexyl Triazone | 2.0 | | 2.0 | | 2.0 | | 2.0 | | |
| | Bis-Ethylhexyloxy-phenol Methoxyphenyl Triazine | 1.0 | 1.0 | 1.0 | 1.0 | 2.0 | 2.0 | 1.0 | 1.0 | 2.0 |
| Part B | Butylene Glycol | 3.0 | 3.0 | 3.0 | 3.0 | 3.0 | 3.0 | 3.0 | 3.0 | 3.0 |
| | Polyglyceryl-3 Disiloxane Dimethicone | 0.6 | 0.6 | 0.6 | 0.6 | 0.6 | 0.6 | 0.6 | 0.6 | 0.6 |
| | Polyglyceryl-3 Polydimethylsiloxy ethyl Dimethicone | 0.3 | 0.3 | 0.3 | 0.3 | 0.3 | 0.3 | 0.3 | 0.3 | 0.3 |
| | Acrylamide/Sodium Acryloyldimethyl-taurate Copolymer (and) Isohexadecane (and) Polysorbate 80 | 0.6 | 0.6 | 0.6 | 0.6 | 0.6 | 0.6 | 0.6 | 0.6 | 0.6 |
| | Ammonium Acryloyldimethyl-taurate/VP Copolymer | 0.7 | 0.7 | 0.7 | 0.7 | 0.7 | 0.7 | 0.7 | 0.7 | 0.7 |

| INCI name | A % w/w | B % w/w | C % w/w | D % w/w | E % w/w | F % w/w | G % w/w | H % w/w | I % w/w |
|---|---|---|---|---|---|---|---|---|---|
| Sodium Chloride | 0.1 | 0.1 | 0.1 | 0.1 | 0.1 | 0.1 | 0.1 | 0.1 | 0.1 |
| Aqua | qs to 100 | qs to 100 | qs to 100 | qs to 100 | qs to 100 | qs to 100 | qs to 100 | qs to 100 | qs to 100 |
| Methylene Bis-Benzotriazolyl Tetramethylbutyl-phenol * | 3.0 | 3.0 | 3.0 | 3.0 | 3.0 | 3.0 | 3.0 | 3.0 | 3.0 |
| Bis-Ethylhexyloxyphenol Methoxyphenyl Triazine ** | 1.0 | 1.0 | 1.0 | 1.0 | | | 1.0 | 1.0 | |
| Tris-Biphenyl Triazine * | 1.0 | 1.0 | 1.0 | | | | | | |
| Methanone, 1,1'-(1,4-piperazinediyl)bis[1-[2-[4-(diethylamino)-2-hydroxybenzoyl]phenyl] CAS number (919803-06-8) * | 1.0 | 1.0 | 1.0 | 1.0 | 1.0 | 1.0 | 1.0 | 1.0 | |
| Phenyl-benzimidazole Sulfonic Acid | 0.0 | | | | | | 2.0 | 2.0 | 2.0 |
| Copolymer 1 | 2.0 | 2.0 | 2.0 | 2.0 | 2.0 | 2.0 | 2.0 | 2.0 | 2.0 |

Water-resistant "Cream-to-powder" Formulations

| INCI name | A % w/w | B % w/w | C % w/w | D % w/w | E % w/w | F % w/w | G % w/w | H % w/w | I % w/w |
|---|---|---|---|---|---|---|---|---|---|
| Isoeicosane | 10.0 | 10.0 | 10.0 | 10.0 | 10.0 | 10.0 | 10.0 | 10.0 | 10.0 |
| Polyisobutene | 2.0 | 2.0 | 2.0 | 2.0 | 2.0 | 2.0 | 2.0 | 2.0 | 2.0 |
| Phenethyl Benzoate | 4.0 | 4.0 | 4.0 | 4.0 | 4.0 | 4.0 | 4.0 | 4.0 | 4.0 |
| Tridecyl Trimellitate | 2.0 | 2.0 | 2.0 | 2.0 | 2.0 | 2.0 | 2.0 | 2.0 | 2.0 |
| Triisodecyl Trimellitate | 2.0 | 2.0 | 2.0 | 2.0 | 2.0 | 2.0 | 2.0 | 2.0 | 2.0 |
| Propylene Glycol Dicaprylate/Dicaprate | 1.0 | 1.0 | 1.0 | 1.0 | 1.0 | 1.0 | 1.0 | 1.0 | 1.0 |
| Cetearyl Ethylhexanoate | 20.5 | 20.5 | 20.5 | 20.5 | 20.5 | 20.5 | 20.5 | 20.5 | 20.5 |
| Oleyl alcohol | 5.0 | 5.0 | 5.0 | 5.0 | 5.0 | 5.0 | 5.0 | 5.0 | 5.0 |
| Ceresin | 4.5 | 4.5 | 4.5 | 4.5 | 4.5 | 4.5 | 4.5 | 4.5 | 4.5 |
| Talc | qsp | qsp | qsp | qsp | qsp | qsp | qsp | qsp | qsp |
| Polyethylene | 4.0 | 4.0 | 4.0 | 4.0 | 4.0 | 4.0 | 4.0 | 4.0 | 4.0 |
| Silica | 10.7 | 10.7 | 10.7 | 10.7 | 10.7 | 10.7 | 10.7 | 10.7 | 10.7 |
| Calcium Aluminum Borosilicate (and) Bismuth Oxychloride | 1.0 | 1.0 | 1.0 | 1.0 | 1.0 | 1.0 | 1.0 | 1.0 | 1.0 |
| Iron Oxides | 3.4 | 3.4 | 3.4 | 3.4 | 3.4 | 3.4 | 3.4 | 3.4 | 3.4 |
| Tocopheryl Acetate | 0.3 | 0.3 | 0.3 | 0.3 | 0.3 | 0.3 | 0.3 | 0.3 | 0.3 |
| Diethylamino Hydroxy Benzoyl Hexyl Benzoate | 4.0 | 4.0 | 4.0 | 4.0 | 4.0 | 4.0 | 4.0 | 4.0 | 4.0 |
| Ethylhexyl Triazone | 2.0 | 2.0 | | | 2.0 | 2.0 | 2.0 | | |
| Ethylhexyl Methoxycinnamate | 7.0 | 7.0 | | | | | | | |
| Bis-Ethylhexyloxyphenol Methoxyphenyl Triazine | 0.0 | 2.0 | | 2.0 | | 2.0 | 2.0 | | 2.0 |
| Methylene Bis-Benzotriazolyl Tetramethylbutyl-phenol * | 3.0 | 3.0 | | | 3.0 | 3.0 | | 3.0 | 3.0 |
| Malonates of the formula (C) or (D) | 0.0 | 10.0 | 10.0 | 10.0 | 10.0 | 10.0 | 10.0 | 10.0 | |

| INCI name | A % w/w | B % w/w | C % w/w | D % w/w | E % w/w | F % w/w | G % w/w | H % w/w | I % w/w |
|---|---|---|---|---|---|---|---|---|---|
| Titanium Dioxide *** | 2.0 | 2.0 | 2.0 | 2.0 | 2.0 | 2.0 | 2.0 | 2.0 | 2.0 |
| Copolymer 1 | 2.0 | 2.0 | 2.0 | 2.0 | 2.0 | 2.0 | 2.0 | 2.0 | 2.0 |

Water-resistant "Hydrous Gel" Formulations

| INCI | A % w/w | B % w/w | C % w/w | D % w/w | E % w/w | F % w/w | G % w/w | H % w/w | I % w/w |
|---|---|---|---|---|---|---|---|---|---|
| Dimethicone copolyol | 0.2 | 0.2 | 0.2 | 0.2 | 0.2 | 0.2 | 0.2 | 0.2 | 0.2 |
| Colorant/lakes | 0.6 | 0.6 | 0.6 | 0.6 | 0.6 | 0.6 | 0.6 | 0.6 | 0.6 |
| Mica | 1.3 | 1.3 | 1.3 | 1.3 | 1.3 | 1.3 | 1.3 | 1.3 | 1.3 |
| Butylene Glycol | 2.0 | 2.0 | 2.0 | 2.0 | 2.0 | 2.0 | 2.0 | 2.0 | 2.0 |
| Aqua | qs to 100 | qs to 100 | qs to 100 | qs to 100 | qs to 100 | qs to 100 | qs to 100 | qs to 100 | qs to 100 |
| Xanthan Gum | 0.2 | 0.2 | 0.2 | 0.2 | 0.2 | 0.2 | 0.2 | 0.2 | 0.2 |
| Carbomer 2% solution | 20.0 | 20.0 | 20.0 | 20.0 | 20.0 | 20.0 | 20.0 | 20.0 | 20.0 |
| Disodium EDTA | 0.1 | 0.1 | 0.1 | 0.1 | 0.1 | 0.1 | 0.1 | 0.1 | 0.1 |
| PEG-8 | 3.0 | 3.0 | 3.0 | 3.0 | 3.0 | 3.0 | 3.0 | 3.0 | 3.0 |
| Panthenol. 50% in Propylene Glycol | 1.0 | 1.0 | 1.0 | 1.0 | 1.0 | 1.0 | 1.0 | 1.0 | 1.0 |
| VP/VA Copolymer | 7.0 | 7.0 | 7.0 | 7.0 | 7.0 | 7.0 | 7.0 | 7.0 | 7.0 |
| Tetrahydroxypropyl Ethylenediamine | 0.8 | 0.8 | 0.8 | 0.8 | 0.8 | 0.8 | 0.8 | 0.8 | 0.8 |
| Preservative | qs | qs | qs | qs | qs | qs | qs | qs | qs |
| Methylene Bis-Benzotriazolyl Tetramethylbutylphenol * | 0.0 | | | | 3.0 | 3.0 | 3.0 | 3.0 | |
| Bis-Ethylhexyloxyphenol Methoxyphenyl Triazine ** | 2.0 | 2.0 | 2.0 | 2.0 | 2.0 | 2.0 | 2.0 | 2.0 | 2.0 |
| Copolymer 1 | 2.0 | 2.0 | 2.0 | 2.0 | 2.0 | 2.0 | 2.0 | 2.0 | 2.0 |

Water-resistant Powder Make-up Formulations

| INCI name | A % w/w | B % w/w | C % w/w | D % w/w | E % w/w | F % w/w | G % w/w | H % w/w | I % w/w |
|---|---|---|---|---|---|---|---|---|---|
| Lauroyl Lysine | 10.0 | 10.0 | 10.0 | 10.0 | 10.0 | 10.0 | 10.0 | 10.0 | 10.0 |
| Isononyl Isononanoate | 3.0 | 3.0 | 3.0 | 3.0 | 3.0 | 3.0 | 3.0 | 3.0 | 3.0 |
| Phenethyl Benzoate | 1.0 | 1.0 | 1.0 | 1.0 | 1.0 | 1.0 | 1.0 | 1.0 | 1.0 |
| Tridecyl Trimellitate | 1.0 | 1.0 | 1.0 | 1.0 | 1.0 | 1.0 | 1.0 | 1.0 | 1.0 |
| Triisodecyl Trimellitate | 1.0 | 1.0 | 1.0 | 1.0 | 1.0 | 1.0 | 1.0 | 1.0 | 1.0 |
| Isopropyl Lauroyl Sarcosinate | 0.5 | 0.5 | 0.5 | 0.5 | 0.5 | 0.5 | 0.5 | 0.5 | 0.5 |
| Isododecane | 3.0 | 3.0 | 3.0 | 3.0 | 3.0 | 3.0 | 3.0 | 3.0 | 3.0 |
| Zinc Laurate | 5.0 | 5.0 | 5.0 | 5.0 | 5.0 | 5.0 | 5.0 | 5.0 | 5.0 |
| Sorbitan Sesquioleate | 0.5 | 0.5 | 0.5 | 0.5 | 0.5 | 0.5 | 0.5 | 0.5 | 0.5 |
| Sorbitan Isostearate | 0.2 | 0.2 | 0.2 | 0.2 | 0.2 | 0.2 | 0.2 | 0.2 | 0.2 |
| Dimethicone | 1.0 | 1.0 | 1.0 | 1.0 | 1.0 | 1.0 | 1.0 | 1.0 | 1.0 |
| Talc | qsp | qsp | qsp | qsp | qsp | qsp | qsp | qsp | qsp |
| Polyethylene | 1.0 | 1.0 | 1.0 | 1.0 | 1.0 | 1.0 | 1.0 | 1.0 | 1.0 |
| PTFE | 3.0 | 3.0 | 3.0 | 3.0 | 3.0 | 3.0 | 3.0 | 3.0 | 3.0 |
| Sericite | 20.0 | 20.0 | 20.0 | 20.0 | 20.0 | 20.0 | 20.0 | 20.0 | 20.0 |
| Yellow Iron Oxide | 1.7 | 1.7 | 1.7 | 1.7 | 1.7 | 1.7 | 1.7 | 1.7 | 1.7 |
| Red Iron Oxide | 0.5 | 0.5 | 0.5 | 0.5 | 0.5 | 0.5 | 0.5 | 0.5 | 0.5 |
| Black Iron Oxide | 0.2 | 0.2 | 0.2 | 0.2 | 0.2 | 0.2 | 0.2 | 0.2 | 0.2 |
| Polymethyl Methacrylate (spherical) | 10.0 | 10.0 | 10.0 | 10.0 | 10.0 | 10.0 | 10.0 | 10.0 | 10.0 |

| INCI name | A % w/w | B % w/w | C % w/w | D % w/w | E % w/w | F % w/w | G % w/w | H % w/w | I % w/w |
|---|---|---|---|---|---|---|---|---|---|
| Methylene Bis-Benzotriazolyl Tetramethylbutyl-phenol * | 3.0 | 3.0 | 3.0 | 3.0 | 3.0 | | | 3.0 | 2.0 |
| Titanium Dioxide *** | 0.0 | 2.0 | | | 2.0 | 2.0 | 2.0 | 2.0 | 1.0 |
| Tris-Biphenyl Triazine * | 0.0 | | 2.0 | | 1.0 | | | | 1.0 |
| Bis-Ethylhexyloxy-phenol Methoxyphenyl Triazine ** | 0.0 | | | 2.0 | | | | | 1.0 |
| Methanone, 1,1'-(1,4-piperazine-diyl)bis[1-[2-[4-(diethylamino)-2-hydroxybenzoyl]phenyl]-CAS number (919803-06-8) * | 0.0 | | | | | 2.0 | | 2.0 | 1.0 |
| Zinc Oxide *** | | | | | | | 2.0 | | 1.0 |
| Copolymer 1 | 2.0 | 2.0 | 2.0 | 2.0 | 2.0 | 2.0 | 2.0 | 2.0 | 2.0 |

Water-resistant Oil-in-water Make-up Formulations

| INCI name | A % w/w | B % w/w | C % w/w | D % w/w | E % w/w | F % w/w | G % w/w | H % w/w | I % w/w |
|---|---|---|---|---|---|---|---|---|---|
| Butylene Glycol | 6.5 | 6.5 | 6.5 | 6.5 | 6.5 | 6.5 | 6.5 | 6.5 | 6.5 |
| Magnesium Aluminum Silicate | 0.5 | 0.5 | 0.5 | 0.5 | 0.5 | 0.5 | 0.5 | 0.5 | 0.5 |
| Cellulose Gum | 0.3 | 0.3 | 0.3 | 0.3 | 0.3 | 0.3 | 0.3 | 0.3 | 0.3 |
| Xanthan Gum | 0.1 | 0.1 | 0.1 | 0.1 | 0.1 | 0.1 | 0.1 | 0.1 | 0.1 |
| Triethanolamine | 1.0 | 1.0 | 1.0 | 1.0 | 1.0 | 1.0 | 1.0 | 1.0 | 1.0 |
| Polysorbate 20 | 0.3 | 0.3 | 0.3 | 0.3 | 0.3 | 0.3 | 0.3 | 0.3 | 0.3 |
| Sericite | 7.0 | 7.0 | 7.0 | 7.0 | 7.0 | 7.0 | 7.0 | 7.0 | 7.0 |
| Iron Oxides | 1.1 | 1.1 | 1.1 | 1.1 | 1.1 | 1.1 | 1.1 | 1.1 | 1.1 |
| Silica (spherical) | 1.0 | 1.0 | 1.0 | 1.0 | 1.0 | 1.0 | 1.0 | 1.0 | 1.0 |
| Cetearyl Ethylhexanoate | 10.0 | 10.0 | 10.0 | 10.0 | 10.0 | 10.0 | 10.0 | 10.0 | 10.0 |
| Stearic Acid | 2.5 | 2.5 | 2.5 | 2.5 | 2.5 | 2.5 | 2.5 | 2.5 | 2.5 |
| Glyceryl stearate | 2.0 | 2.0 | 2.0 | 2.0 | 2.0 | 2.0 | 2.0 | 2.0 | 2.0 |
| Tridecyl Trimellitate | 2.0 | 2.0 | 2.0 | 2.0 | 2.0 | 2.0 | 2.0 | 2.0 | 2.0 |
| Aqua | qsp | qsp | qsp | qsp | qsp | qsp | qsp | qsp | qsp |
| Preservative | 0.6 | 0.6 | 0.6 | 0.6 | 0.6 | 0.6 | 0.6 | 0.6 | 0.6 |
| Diethylamino Hydroxy Benzoyl Hexyl Benzoate | 2.0 | 2.0 | 2.0 | 2.0 | 2.0 | 2.0 | 2.0 | 2.0 | 2.0 |
| Ethylhexyl Triazone | 2.0 | 2.0 | | | | | 2.0 | 2.0 | 2.0 |
| Ethylhexyl Methoxycinnamate | 7.0 | 7.0 | 7.0 | 7.0 | 7.0 | | | | |
| Bis-Ethylhexyloxy-phenol Methoxyphenyl Triazine | 0.0 | 2.0 | | 2.0 | | 2.0 | 2.0 | | 2.0 |
| Methylene Bis-Benzotriazolyl Tetramethylbutyl-phenol * | 0.0 | | | | | | | | 2.0 |
| Malonates of formula (C) or (D) | 0.0 | | | | | 10.0 | 10.0 | 10.0 | |
| Tris-Biphenyl Triazine * | 1.0 | 1.0 | 1.0 | 1.0 | 1.0 | 1.0 | 1.0 | 1.0 | |
| Ethylhexyl Salicylate | 5.0 | | | | | | | | 5.0 |
| Diethylhexyl Butamido Triazone | 0.0 | 1.0 | | | | | | | 1.0 |
| Phenylbenzimidazole Sulfonic Acid | 0.0 | 2.0 | | | | | | | 2.0 |

-continued

| INCI name | A % w/w | B % w/w | C % w/w | D % w/w | E % w/w | F % w/w | G % w/w | H % w/w | I % w/w |
|---|---|---|---|---|---|---|---|---|---|
| Titanium Dioxide *** | 0.0 | | | 2.0 | | | | | |
| Homosalate | 0.0 | | | | 10.0 | | | | 5.0 |
| Copolymer 1 | 2.0 | 2.0 | 2.0 | 2.0 | 2.0 | 2.0 | 2.0 | 2.0 | 2.0 |

Water-resistant Water-free Make-up Formulations

| INCI name | A % w/w | B % w/w | C % w/w | D % w/w | E % w/w | F % w/w | G % w/w | H % w/w | I % w/w |
|---|---|---|---|---|---|---|---|---|---|
| Isononyl Isononanoate | qsp | qsp | qsp | qsp | qsp | qsp | qsp | qsp | qsp |
| Phenethyl Benzoate | 4.0 | 4.0 | 4.0 | 4.0 | 4.0 | 4.0 | 4.0 | 4.0 | 4.0 |
| Tridecyl Trimellitate | 2.0 | 2.0 | 2.0 | 2.0 | 2.0 | 2.0 | 2.0 | 2.0 | 2.0 |
| Triisodecyl Trimellitate | 2.0 | 2.0 | 2.0 | 2.0 | 2.0 | 2.0 | 2.0 | 2.0 | 2.0 |
| Propylene Glycol Dicaprylate/Dicaprate | 1.0 | 1.0 | 1.0 | 1.0 | 1.0 | 1.0 | 1.0 | 1.0 | 1.0 |
| Sorbitan Sesquioleate | 0.5 | 0.5 | 0.5 | 0.5 | 0.5 | 0.5 | 0.5 | 0.5 | 0.5 |
| Cyclopentasiloxane | 15.0 | 15.0 | 15.0 | 15.0 | 15.0 | 15.0 | 15.0 | 15.0 | 15.0 |
| Cylopentasiloxane (and) Quaternium-18 Hectorite | 15.0 | 15.0 | 15.0 | 15.0 | 15.0 | 15.0 | 15.0 | 15.0 | 15.0 |
| Talc | 5.0 | 5.0 | 5.0 | 5.0 | 5.0 | 5.0 | 5.0 | 5.0 | 5.0 |
| Iron Oxides | 2.5 | 2.5 | 2.5 | 2.5 | 2.5 | 2.5 | 2.5 | 2.5 | 2.5 |
| Tocopheryl Acetate | 0.5 | 0.5 | 0.5 | 0.5 | 0.5 | 0.5 | 0.5 | 0.5 | 0.5 |
| Merocyanines of the formula (A) or (B) | 1.0 | 1.0 | 1.0 | 1.0 | 1.0 | 1.0 | 1.0 | 1.0 | 1.0 |
| Diethylamino Hydroxy Benzoyl Hexyl Benzoate | 4.0 | 4.0 | 4.0 | 4.0 | 4.0 | 4.0 | 4.0 | 4.0 | 4.0 |
| Ethylhexyl Triazone | 2.0 | 2.0 | | | | | 2.0 | 2.0 | 2.0 |
| Ethylhexyl Methoxycinnamate | 7.0 | 7.0 | | | | | | | |
| Bis-Ethylhexyloxy-phenol Methoxyphenyl Triazine | 0.0 | 2.0 | | 2.0 | | 2.0 | 2.0 | | 2.0 |
| Malonates of the formula (C) or (D) | 0.0 | | 10.0 | 10.0 | 10.0 | 10.0 | 10.0 | 10.0 | 10.0 |
| Copolymer 1 | 2.0 | 2.0 | 2.0 | 2.0 | 2.0 | 2.0 | 2.0 | 2.0 | 2.0 |

Water-resistant PIT Sunscreen Sprays

| INCI name | A % w/w | B % w/w | C % w/w | D % w/w | E % w/w | F % w/w | G % w/w | H % w/w | I % w/w |
|---|---|---|---|---|---|---|---|---|---|
| Glyceryl Stearate | 0.5 | 0.5 | 0.5 | 0.5 | 0.5 | 0.5 | 0.5 | 0.5 | 0.5 |
| Ceteareth-20 | 4.0 | 4.0 | 4.0 | 4.0 | 4.0 | 4.0 | 4.0 | 4.0 | 4.0 |
| Cetyl Alcohol | 2.5 | 2.5 | 2.5 | 2.5 | 2.5 | 2.5 | 2.5 | 2.5 | 2.5 |
| Cetyl PEG/PPG-10/1 Dimethicone | 1.0 | 1.0 | 1.0 | 1.0 | 1.0 | 1.0 | 1.0 | 1.0 | 1.0 |
| Phenethyl Benzoate | 4.0 | 4.0 | 4.0 | 4.0 | 4.0 | 4.0 | 4.0 | 4.0 | 4.0 |
| Triisodecyl Trimellitate | 2.0 | 2.0 | 2.0 | 2.0 | 2.0 | 2.0 | 2.0 | 2.0 | 2.0 |
| Triheptanoin | 1.0 | 1.0 | 1.0 | 1.0 | 1.0 | 1.0 | 1.0 | 1.0 | 1.0 |
| C12-15 Alkyl Benzoate | 2.0 | 2.0 | 2.0 | 2.0 | 2.0 | 2.0 | 2.0 | 2.0 | 2.0 |
| Cocoglycerides | 4.0 | 4.0 | 4.0 | 4.0 | 4.0 | 4.0 | 4.0 | 4.0 | 4.0 |
| Butylene Glycol Dicaprylate/Dicaprate | 5.0 | 5.0 | 5.0 | 5.0 | 5.0 | 5.0 | 5.0 | 5.0 | 5.0 |
| Phenyltrimethicone | 2.0 | 2.0 | 2.0 | 2.0 | 2.0 | 2.0 | 2.0 | 2.0 | 2.0 |
| Glycerin | 3.0 | 3.0 | 3.0 | 3.0 | 3.0 | 3.0 | 3.0 | 3.0 | 3.0 |
| Vitamin E Acetate | 0.5 | 0.5 | 0.5 | 0.5 | 0.5 | 0.5 | 0.5 | 0.5 | 0.5 |
| PTFE | 0.3 | 0.3 | 0.3 | 0.3 | 0.3 | 0.3 | 0.3 | 0.3 | 0.3 |
| Trisodium EDTA | 1.0 | 1.0 | 1.0 | 1.0 | 1.0 | 1.0 | 1.0 | 1.0 | 1.0 |

| INCI name | A % w/w | B % w/w | C % w/w | D % w/w | E % w/w | F % w/w | G % w/w | H % w/w | I % w/w |
|---|---|---|---|---|---|---|---|---|---|
| DMDM Hydantoin | 0.6 | 0.6 | 0.6 | 0.6 | 0.6 | 0.6 | 0.6 | 0.6 | 0.6 |
| Phenoxyethanol | 0.5 | 0.5 | 0.5 | 0.5 | 0.5 | 0.5 | 0.5 | 0.5 | 0.5 |
| Alcohol | 3.0 | 3.0 | 3.0 | 3.0 | 3.0 | 3.0 | 3.0 | 3.0 | 3.0 |
| Fragrance | 0.2 | 0.2 | 0.2 | 0.2 | 0.2 | 0.2 | 0.2 | 0.2 | 0.2 |
| Aqua | ad 100 | ad 100 | ad 100 | ad 100 | ad 100 | ad 100 | ad 100 | ad 100 | ad 100 |
| Bis-Ethylhexyloxyphenol Methoxyphenyl Triazine | 2.0 | 2.0 | | | | 2.0 | | | |
| Methylene Bis-Benzotriazolyl Tetramethylbutyl-phenol * | 3.0 | | 3.0 | | | | 3.0 | | |
| Tris-Biphenyl Triazine * | 2.0 | | | 2.0 | | | | 2.0 | |
| Methanone, 1,1'-(1,4-piperazine-diyl)bis[1-[2-[4-(diethylamino)-2-hydroxybenzoyl]phenyl]-CAS number (919803-06-8) * | 2.0 | | | | 2.0 | | | | 2.0 |
| Benzophenone-3 | 3.0 | | | | | 3.0 | 3.0 | 3.0 | 3.0 |
| Homosalate | 10.0 | 10.0 | 10.0 | 10.0 | 10.0 | 10.0 | 10.0 | 10.0 | 10.0 |
| Octocrylene | 8.0 | 8.0 | 8.0 | 8.0 | 8.0 | 8.0 | 8.0 | 8.0 | 8.0 |
| Ethylhexyl Salicylate | 5.0 | 5.0 | 5.0 | 5.0 | 5.0 | 5.0 | 5.0 | 5.0 | 5.0 |
| Butyl Methoxydibenzoyl methane | 3.0 | 3.0 | 3.0 | 3.0 | 3.0 | 3.0 | 3.0 | 3.0 | 3.0 |
| Copolymer 1 | 2.0 | 2.0 | 2.0 | 2.0 | 2.0 | 2.0 | 2.0 | 2.0 | 2.0 |

Water-resistant "Pickering" Lotions

| INCI name | A % w/w | B % w/w | C % w/w | D % w/w | E % w/w | F % w/w | G % w/w | H % w/w | I % w/w |
|---|---|---|---|---|---|---|---|---|---|
| Mineral Oil | 16.0 | 16.0 | 16.0 | 16.0 | 16.0 | 16.0 | 16.0 | 16.0 | 16.0 |
| Octyldodecanol | 5.0 | 5.0 | 5.0 | 5.0 | 5.0 | 5.0 | 5.0 | 5.0 | 5.0 |
| Caprylic/Capric Triglyceride | 6.0 | 6.0 | 6.0 | 6.0 | 6.0 | 6.0 | 6.0 | 6.0 | 6.0 |
| Hydroxyoctacosanyl Hydroxystearate | 1.5 | 1.5 | 1.5 | 1.5 | 1.5 | 1.5 | 1.5 | 1.5 | 1.5 |
| Disteardimonium Hectorite | 1.0 | 1.0 | 1.0 | 1.0 | 1.0 | 1.0 | 1.0 | 1.0 | 1.0 |
| Cyclomethicone | 2.0 | 2.0 | 2.0 | 2.0 | 2.0 | 2.0 | 2.0 | 2.0 | 2.0 |
| Silica Dimethyl Silylate | 0.5 | 0.5 | 0.5 | 0.5 | 0.5 | 0.5 | 0.5 | 0.5 | 0.5 |
| Magnesium Sulfate | 0.7 | 0.7 | 0.7 | 0.7 | 0.7 | 0.7 | 0.7 | 0.7 | 0.7 |
| Glycerin | 3.0 | 3.0 | 3.0 | 3.0 | 3.0 | 3.0 | 3.0 | 3.0 | 3.0 |
| Butylene Glycol | 5.0 | 5.0 | 5.0 | 5.0 | 5.0 | 5.0 | 5.0 | 5.0 | 5.0 |
| Trisodium EDTA | 1.0 | 1.0 | 1.0 | 1.0 | 1.0 | 1.0 | 1.0 | 1.0 | 1.0 |
| Propylene Carbonate | 0.3 | 0.3 | 0.3 | 0.3 | 0.3 | 0.3 | 0.3 | 0.3 | 0.3 |
| Glucosylrutin (and) Methylparaben | 0.2 | 0.2 | 0.2 | 0.2 | 0.2 | 0.2 | 0.2 | 0.2 | 0.2 |
| Propylparaben | 0.1 | 0.1 | 0.1 | 0.1 | 0.1 | 0.1 | 0.1 | 0.1 | 0.1 |
| Phenoxyethanol | 0.5 | 0.5 | 0.5 | 0.5 | 0.5 | 0.5 | 0.5 | 0.5 | 0.5 |
| Aqua | ad 100 | ad 100 | ad 100 | ad 100 | ad 100 | ad 100 | ad 100 | ad 100 | ad 100 |
| Diethylamino Hydroxy Benzoyl Hexyl Benzoate | 4.0 | 4.0 | 4.0 | 4.0 | 4.0 | 4.0 | 4.0 | 4.0 | 4.0 |
| Ethylhexyl Triazone | 2.0 | | 2.0 | | 2.0 | | 2.0 | | 2.0 |
| Ethylhexyl Methoxycinnamate | 0.0 | 7.0 | | 7.0 | | 7.0 | | 7.0 | 7.0 |
| Bis-Ethylhexyloxyphenol Methoxyphenyl Triazine | 0.0 | 2.0 | 2.0 | | | 2.0 | | 2.0 | 2.0 |

-continued

| INCI name | A % w/w | B % w/w | C % w/w | D % w/w | E % w/w | F % w/w | G % w/w | H % w/w | I % w/w |
|---|---|---|---|---|---|---|---|---|---|
| Methylene Bis-Benzotriazolyl Tetramethylbutylphenol * | 0.0 | | | | 3.0 | 3.0 | 3.0 | 3.0 | |
| Isoamyl p-Methoxycinnamate | 10.0 | 10.0 | 10.0 | 10.0 | 10.0 | 10.0 | 10.0 | 10.0 | 10.0 |
| 4-Methylbenzylidene Camphor | 8.0 | 8.0 | 8.0 | 8.0 | 8.0 | 8.0 | 8.0 | 8.0 | 8.0 |
| Polysilicone-15 | 5.0 | 5.0 | 5.0 | 5.0 | 5.0 | 5.0 | 5.0 | 5.0 | 5.0 |
| Disodium Phenyl Dibenzylmidazole Tetrasulfonate | 3.0 | 3.0 | 3.0 | 3.0 | 3.0 | 3.0 | 3.0 | 3.0 | 3.0 |
| Copolymer 1 | 2.0 | 2.0 | 2.0 | 2.0 | 2.0 | 2.0 | 2.0 | 2.0 | 2.0 |

Water-resistant Mascaras

| Phases | Products | INCI | % by weight |
|---|---|---|---|
| A | Versagel MC1600 | Isohexadecane (and) Butylene/Ethylene/Styrene Copolymer (and) Ethylene/Propylene/Styrene Copolymer | 70.46 |
| | Copolymer 1 | | 2.00 |
| | Aerosil R812S | Silica Silycate | 1.45 |
| | Silshine 151 | Phenylpropyldimethylsiloxysilicate | 1.00 |
| | SS4230 | Cyclopentasiloxane (and) Trimethylsiloxysilicate | 4.80 |
| | Preservatives | Preservatives | q.s. |
| B | Cloisonné® Nu-Antique Blue 626CB | Mica (and) Titanium Dioxide (and) Iron Oxides (and) Ferric Ferrocyanide) | 9.67 |
| | Reflecks™ Dimensions Beams of Blue G630L | (Calcium Sodium Borosilicate (and) Titanium Dioxide (and) Ferric Ferrocyanide) | 3.86 |
| | Reflecks™ Dimensions Beams of Blue G630L | (Calcium Sodium Borosilicate (and) Titanium Dioxide) | 6.76 |

The invention claimed is:

1. A method for improving the water resistance of a cosmetic formulation comprising the step of adding thereto a copolymer comprising
   a) 60 to 80% by weight of N-vinylpyrrolidone and
   b) 20 to 40% by weight of a hydrophobically modified acrylic acid derivative,
   wherein the copolymer comprises more than 99% by weight of N-vinylpyrrolidone and the hydrophobically modified acrylic acid derivative.

2. The method according to claim 1, where the hydrophobically modified acrylic acid derivative is an acrylic acid ester or methacrylic acid ester of the formula I,

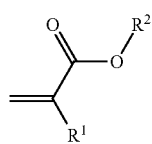

(I)

in which
   $R^1$ is hydrogen or methyl and
   $R^2$ is $C_8$ to $C_{32}$-alkyl.

3. The method according to claim 1, where the cosmetic formulation comprises at least one water-soluble, water-insoluble or sparingly water-soluble active ingredient or effect substance.

4. The method according to claim 1, where the cosmetic formulation is a sunscreen composition or a make-up composition for the eyes, the lips or the face.

5. The method according to claim 1,
   wherein the cosmetic formulation is a sunscreen and further comprises at least one UV filter for increasing the sun protection factor of the sunscreen.

6. A cosmetic formulation selected from the group consisting of sunscreen compositions and make-up compositions for the eyes, the lips or the face, comprising:
   at least one water-insoluble or sparingly water-soluble active ingredient or effect substance and at least one copolymer comprising:
   a) 60 to 80% by weight of N-vinylpyrrolidone and
   b) 20 to 40% by weight of a hydrophobically modified acrylic acid derivative,
   wherein the at least one copolymer comprises more than 99% by weight of N-vinylpyrrolidone and the hydrophobically modified acrylic acid derivative.

7. A sunscreen formulation comprising at least one UV filter and at least one copolymer comprising:
   a) 60 to 80% by weight of N-vinylpyrrolidone and
   b) 20 to 40% by weight of a hydrophobically modified acrylic acid derivative,
   wherein the at least one copolymer comprises more than 99% by weight of N-vinylpyrrolidone and the hydrophobically modified acrylic acid derivative.

8. A make-up composition for the eyes, the lips or the face, comprising at least one dye, one pigment or one effect pigment and at least one copolymer comprising
   a) 60 to 80% by weight of N-vinylpyrrolidone and
   b) 20 to 40% by weight of a hydrophobically modified acrylic acid derivative,
   wherein the at least one copolymer comprises more than 99% by weight of N-vinylpyrrolidone and the hydrophobically modified acrylic acid derivative.

9. The formulation according to claim 6,
   where the hydrophobically modified acrylic acid derivative is an acrylic acid ester or methacrylic acid ester of the formula I,

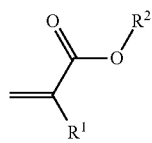 (I)

in which
$R^1$ is hydrogen or methyl and
$R^2$ is $C_8$ to $C_{32}$-alkyl.

10. The cosmetic formulation according to claim 6, wherein the concentration of the at least one copolymer in the cosmetic formulation ranges from 0.1 to 10 wt % of the total cosmetic formulation.

11. The sunscreen formulation according to claim 7, wherein the concentration of the at least one copolymer in sunscreen formulation ranges from 0.1 to 10 wt % of the total cosmetic formulation.

12. The make-up composition according to claim 8, wherein the concentration of the at least one copolymer in the make-up compositions ranges from 0.1 to 10 wt % of the total make-up composition.

13. The formulation according to claim 9, wherein
$R^1$ is hydrogen or methyl and
$R^2$ is $C_{12}$ to $C_{24}$-alkyl.

* * * * *